United States Patent
Fossum et al.

(10) Patent No.: US 7,517,586 B2
(45) Date of Patent: Apr. 14, 2009

(54) ABSORBENT STRUCTURES COMPRISING COATED WATER-SWELLABLE MATERIAL

(75) Inventors: Renae Dianna Fossum, Middletown, OH (US); Mattias Schmidt, Idstein (DE); Axel Meyer, Frankfurt am Main (DE)

(73) Assignee: Procter & Gamble Company, Cincinnati, OH (US)

( * ) Notice: Subject to any disclaimer, the term of this patent is extended or adjusted under 35 U.S.C. 154(b) by 278 days.

(21) Appl. No.: 10/911,912

(22) Filed: Aug. 5, 2004

(65) Prior Publication Data
US 2005/0033255 A1 Feb. 10, 2005

Related U.S. Application Data

(60) Provisional application No. 60/492,899, filed on Aug. 6, 2003, provisional application No. 60/492,819, filed on Aug. 6, 2003.

(51) Int. Cl.
*B32B 15/02* (2006.01)
(52) U.S. Cl. .................. 428/402; 428/403; 428/407
(58) Field of Classification Search .............. 428/423.1, 428/402, 403, 407
See application file for complete search history.

(56) References Cited

U.S. PATENT DOCUMENTS

| | | | |
|---|---|---|---|
| 4,062,817 A | 12/1977 | Westerman | |
| 4,093,776 A | 6/1978 | Aoki et al. | |
| 4,156,664 A | 5/1979 | Skinner et al. | |
| 4,392,908 A | 7/1983 | Dehnel | |
| 4,507,413 A * | 3/1985 | Thoma et al. | 524/42 |
| 4,541,871 A | 9/1985 | Obayashi et al. | |
| 4,625,001 A | 11/1986 | Tsubakimoto et al. | |
| 4,666,983 A | 5/1987 | Tsubakimoto et al. | |
| 4,734,445 A | 3/1988 | Noda et al. | |
| RE32,649 E | 4/1988 | Brandt et al. | |
| 4,824,901 A | 4/1989 | Alexander et al. | |
| 4,835,211 A | 5/1989 | Noda et al. | |
| 4,977,892 A * | 12/1990 | Ewall | 602/52 |
| 5,140,076 A | 8/1992 | Hatsuda et al. | |
| 5,164,459 A | 11/1992 | Kimura et al. | |
| 5,470,964 A | 11/1995 | Qin | |
| 5,562,646 A | 10/1996 | Goldman et al. | |
| 5,633,316 A | 5/1997 | Gartner et al. | |
| 5,714,156 A | 2/1998 | Schmidt et al. | |
| 5,731,365 A | 3/1998 | Engelhardt et al. | |
| 5,783,209 A * | 7/1998 | Imamura et al. | 424/448 |
| 5,840,329 A | 11/1998 | Bai | |
| 5,849,816 A | 12/1998 | Suskind et al. | |
| 5,851,672 A | 12/1998 | Wang et al. | |
| 6,150,469 A | 11/2000 | Harada et al. | |
| 6,239,230 B1 | 5/2001 | Eckert et al. | |
| 6,376,011 B1 | 4/2002 | Reeves et al. | |
| 6,376,618 B1 | 4/2002 | Mitchell et al. | |
| 6,387,495 B1 | 5/2002 | Reeves et al. | |
| 6,391,451 B1 | 5/2002 | Mitchell et al. | |
| 6,534,572 B1 | 3/2003 | Ahmed et al. | |
| 7,049,000 B2 * | 5/2006 | Fossum et al. | 428/402 |
| 2002/0128618 A1 | 9/2002 | Frenz et al. | |

FOREIGN PATENT DOCUMENTS

| | | |
|---|---|---|
| EP | 0 799 258 B1 | 10/1997 |
| JP | 56 159232 A | 12/1981 |
| WO | WO 90/08789 A1 | 8/1990 |
| WO | WO 92/16565 A1 | 10/1992 |
| WO | WO 93/05080 A1 | 3/1993 |
| WO | WO 96/14885 A1 | 5/1996 |
| WO | WO 03/043670 A1 | 5/2003 |

* cited by examiner

*Primary Examiner*—Thao T. Tran
(74) *Attorney, Agent, or Firm*—Sarah Ann Dressel; John P. Colbert; John G. Powell

(57) ABSTRACT

This invention relates to an absorbent structure that comprises water-swellable material, which comprises water-swellable polymers that are coated with a coating agent said coating agent comprising a phase-separating elastomeric material, which allows swelling of the water-swellable polymers, without breakage of the coating.

9 Claims, No Drawings

ABSORBENT STRUCTURES COMPRISING COATED WATER-SWELLABLE MATERIAL

CROSS REFERENCE TO RELATED APPLICATIONS

This application claims the benefit of U.S. Provisional Application Nos. 60/492,899 and 60/492,819, filed Aug. 6, 2003.

FIELD OF THE INVENTION

This invention relates to absorbent structures comprising water-swellable material that contains coated water-swellable polymers, namely coated with a coating agent that comprises a phase-separating elastomeric material, which allows swelling of the water-swellable polymers, without breakage of the coating.

BACKGROUND OF THE INVENTION

An important component of disposable absorbent articles such as diapers is an absorbent core structure comprising water-swellable polymers, typically hydrogel-forming water-swellable polymers, also referred to as absorbent gelling material, AGM, or super-absorbent polymers, or SAP's. This polymer material ensures that large amounts of bodily fluids, e.g., urine, can be absorbed by the article during its use and locked away, thus providing low rewet and good skin dryness.

Especially useful water-swellable polymers or SAP's are often made by initially polymerizing unsaturated carboxylic acids or derivatives thereof, such as acrylic acid, alkali metal (e.g., sodium and/or potassium) or ammonium salts of acrylic acid, alkyl acrylates, and the like in the presence of relatively small amounts of di- or poly-functional monomers such as N,N'-methylenebisacrylamide, trimethylolpropane triacrylate, ethylene glycol di(meth)acrylate, or triallylamine. The di- or poly-functional monomer materials serve to lightly cross-link the polymer chains thereby rendering them water-insoluble, yet water-swellable. These lightly crosslinked absorbent polymers contain a multiplicity of carboxylate groups attached to the polymer backbone. It is generally believed, that the neutralized carboxylate groups generate an osmotic driving force for the absorption of body fluids by the crosslinked polymer network.

In addition, the polymer particles are often treated as to form a surface cross-linked layer on the outer surface in order to improve their properties in particular for application in baby diapers.

Water-swellable (hydrogel-forming) polymers useful as absorbents in absorbent members and articles such as disposable diapers need to have adequately high sorption capacity, as well as adequately high gel strength. Sorption capacity needs to be sufficiently high to enable the absorbent polymer to absorb significant amounts of the aqueous body fluids encountered during use of the absorbent article. Together with other properties of the gel, gel strength relates to the tendency of the swollen polymer particles to resist deformation under an applied stress. The gel strength needs to be high enough in the absorbent member or article, so that the particles do not deform and fill the capillary void spaces to an unacceptable degree causing so-called gel blocking. This gel-blocking inhibits the rate of fluid uptake or the fluid distribution, i.e., once gel-blocking occurs, it can substantially impede the distribution of fluids to relatively dry zones or regions in the absorbent article and leakage from the absorbent article can take place well before the water-swellable polymer particles are fully saturated or before the fluid can diffuse or wick past the "blocking" particles into the rest of the absorbent article. Thus, it is important that the water-swellable polymers (when incorporated in an absorbent structure or article) maintain a high wet-porosity and have a high resistance against deformation thus yielding high permeability for fluid transport through the swollen gel bed.

Absorbent polymers with relatively high permeability can be made by increasing the level of internal crosslinking or surface crosslinking, which increases the resistance of the swollen gel against deformation by an external pressure such as the pressure caused by the wearer, but this typically also reduces the absorbent capacity of the gel undesirably.

The inventors have found that often the surface crosslinked water-swellable polymer particles are constrained by the surface-crosslinking 'shell' and cannot absorb and swell sufficiently, and/or that the shell is not strong enough to withstand the stresses of swelling or the stresses associated with performance under load.

The inventors have found that the coatings or shells of the water-swellable polymers, as used in the art, including surface cross-linking 'coatings', break when the polymer swells significantly or that the 'coatings' break after having been in a swollen state for a period of time. They also have found that, as a result thereof, the coated and/or surface-crosslinked water-swellable polymers or super-absorbent material known in the art deform significantly in use thus leading to relatively low porosity and permeability of the gel bed in the wet state. They have found that this could be detrimental to the optimum absorbency, liquid distribution or storage performance of such polymer materials.

Thus, the inventors have found that what is required are water-swellable materials comprising coated water-swellable polymers that have a coating that can exert a force in the wet state and that does not rupture when the polymers swell in body liquid under typical in-use conditions. In the context of this invention, the inventors have found that as a good representative for body liquids such as urine, a 0.9% sodium chloride (saline) by weight in water solution, further called "0.9% saline" can be used. Therefore, the inventors have found that it is required to have coated water-swellable materials where the coating does not substantially rupture when the materials swell in 0.9% saline.

The inventors have found that it is beneficial to coat the water-swellable material with specific elastomeric materials. However, they have found that not all elastomeric materials are suitable in every application as coating agents, because some materials have a good elongation when in a dry state, but not in a wet state.

The inventors have found that, in order to provide the above-described properties and benefits, the elastomeric material should be phase-separating, and typically, it should have at least two different glass transition temperatures, e.g., it typically has at least a first, soft phase with a first glass transition temperature $Tg_1$ and a second, hard component with a second glass transition temperature $Tg_2$.

The inventors have found that when the internal core of the hydrogel polymers swells, this specific coating with phase separating elastomeric polymers extends and remains substantially intact, i.e., without breaking.

It is believed that this is due to the cohesive nature of the elastomeric material and the high elongation to break of the phase-separating material.

The inventors also have found that it is beneficial that the coating around the water-swellable polymers is breathable, as defined herein below, and that the coating that is formed from the coating agent is breathable.

The inventors further found that often the process of applying and/or subsequently treating the coating agents may be important in order to impart high elongation in the wet state.

SUMMARY OF THE INVENTION

The invention provides an absorbent structure, comprising a water-swellable material that comprises water-swellable polymers, coated with a coating agent, wherein said coating agent comprises an elastomeric material that is phase-separating and has at least a first phase with a first glass transition temperature $Tg_1$ and a second phase with a second glass transition temperature $Tg_2$, preferably the difference between $Tg_1$ and $Tg_2$ being at least 30° C.

The invention also provides an absorbent structure comprising water-swellable material that comprises water-swellable polymers, coated with a coating agent, said water-swellable material being obtainable by a process comprising the steps of:
 a) obtaining water-swellable polymer particles;
 b) simultaneously with or subsequently to step a), applying a coating agent to at least a part of said water-swellable polymers particles; and optionally the step of
 c) annealing the resulting coated water-swellable polymer particles of step b), to obtain the water-swellable material,
 whereby said coating agent of step b) comprises an elastomeric phase-separating material that has at least a first phase with a first glass transition temperature $Tg_1$ and a second phase with a second glass transition temperature $Tg_2$, preferably the difference between $Tg_1$ and $Tg_2$ being at least 30° C.

Thus, the invention provides an absorbent structure obtainable by the process of:
 a) obtaining water-swellable polymer particles;
 b) simultaneously with or subsequently to step a), applying said coating agent described herein to at least a part of said water-swellable polymers particles; and optionally the step of:
 c) annealing the resulting coated water-swellable polymer particles of step b),
 d) incorporating the resulting water-swellable material of step b) or c) in an absorbent structure.

The absorbent structure may be a disposable absorbent article, such as a diaper, training pant, sanitary napkin, panty liner or tampon, or the absorbent structure may be part of such absorbent articles, for example the absorbent structure may be the so-called acquisition layer, storage layer and/or absorbent core of a diaper, training pants, sanitary napkin or panty liner.

In general, the elastomeric phase-separating material has a $Tg_1$ of less than room temperature, e.g., less than 25° C., but it is herein preferred that $Tg_1$ is less than 20° C., or even less than 0° C. and a $Tg_2$ is preferably more than room temperature, preferably more than 50° C., or even more than 60° C.

The elastomeric material is preferably a phase-separating block copolymeric material, having a weight average molecular weight of at least 50 kDa, preferably at least 70 kDa, as can be determined by gel permeation chromatography using a multi-angle laser light scattering detector, as known in the art.

The coating agent and/or said elastomeric material is preferably wet-extensible and has a wet-elongation at break (as determined by the test method herein) of at least 400% and a tensile stress at break in the wet state of at least 1 MPa, or even at least 5 MPa, and it preferably has, in the wet state, a wet secant elastic modulus at 400% extension of at least 0.25 MPa, preferably at least 0.50 MPa, more preferably at least about 0.75 MPa, or even at least about 2 MPa, most preferably at least 3 MPa.

Preferably, the coating agent and/or the wet-extensible elastomeric material (made into a film, as set out in the test method below) has, in the dry state, a dry secant modulus at 400% elongation ($SM_{dry400\%}$) and a wet secant modulus at 400% elongation ($SM_{wet400\%}$), whereby the ratio of $SM_{wet400\%}$ to $SM_{dry400\%}$ is between 1.4 to 0.6.

The coating formed from the coating agent is preferably breathable, which means for the purpose of the invention that a film hereof (as described in the MVTR test method set out below) has preferably a moisture vapour transmission rate of at least 800 $g/m^2$/day, or preferably at least 1200 $g/m^2$/day, or even at least 1500 $g/m^2$/day or preferably at least 2100 $g/m^2$/day.

DETAILED DESCRIPTION

Absorbent Structures

The absorbent structure of the invention may be any absorbent structure, used to absorb and retain liquids, such as urine or blood.

The absorbent structure is typically, or forms typically part of, a disposable absorbent article, such as preferably interlabial products, sanitary napkins, panty liners, and preferably adult incontinence products, baby diapers, and training pants.

If the absorbent structure is part of a disposable absorbent article, then the absorbent structure of the invention is typically that part of an absorbent article which serves to store the bodily fluid, e.g., the storage layer of an absorbent article. As known in the art, this may be in direct contact with an acquisition layer, or in one embodiment of the invention, it may form a unitary structure with an acquisition layer.

In yet another embodiment of the invention the absorbent structure is an acquisition layer for use in an absorbent article.

The absorbent structure may be a structure that consists of the water-swellable material and that is then shaped into the required structure, or preferably, it may comprise additional components, such as those used in the art for absorbent structures.

The absorbent structure may comprise the water-swellable material herein at any weight level or concentration. For example, the absorbent structure may also comprise one or more support or wrapping materials, such as foams, films, woven webs and/or nonwoven webs. Preferably, in particular when the absorbent structure is a storage layer of an absorbent article above, or when the absorbent structure comprises a layer that serves as a storage layer, the structure or layer comprises large amounts of the water-swellable material herein, compared to possible other components of the structure, preferably more than 50% by weight of the structure, or even more than 70% by weight, or even more than 80% weight, or even more preferably more than 90% by weight of the structure of the water-swellable material herein, by weight of the structure.

It may alternatively, or in addition, comprise a structuring agent or matrix agent, such as an adhesive, or, for example, the water-swellable material may be mixed with absorbent fibrous material, such as an airfelt material, which can provide a matrix for immobilization of the water-swellable material. However, preferably a relatively low amount of absorbent fibrous (e.g., cellulose) material is used in the absorbent structure. Thus, if the absorbent structure is a liquid storage layer or when the absorbent structure comprises one or more liquid storage layers, it may be preferred that said liquid structure or said liquid storage layer comprises large amounts of the water-swellable material herein and only very little or no absorbent fibers, e.g., preferably less than 40% weight of that layer, or even less than 20% by weight or even less than 10% by weight, or even less than 5% by weight of absorbent fibrous material, and preferably more than 50% or even more than 70% or even more than 80% or even more than 90% by weight of the water-swellable material herein. Preferably, the weight ratio of the water-swellable material to the absorbent fibers, and preferably to any other matrix agents, is at least 1:1, preferably at least 3:2 or even at least 2:1, or even more preferred at least 3:1 or even more preferred at least 4:1.

Preferably the absorbent structure comprises at least a wrapping material, which wraps (the portion comprising) the water-swellable material, a so-called core wrap material. In one preferred embodiment the core wrap material comprises a top layer and a bottom layer, the latter being furthest away from the skin of the user, whereby the core wrap material as a whole or the top layer and/or the bottom layer can be provided from for example a nonwoven material, such as spunbond, meltblown and/or carded nonwovens. One preferred material is a so-called SMS material, comprising a spunbonded, a melt-blown and a further spunbonded layer. Highly preferred are permanently hydrophilic nonwovens, and in particular nonwovens with durably hydrophilic coatings. An alternative preferred material comprises a SMMS-structure. The top layer and the bottom layer may be provided from two or more separate sheets of materials or they may be alternatively provided from a unitary sheet of material Preferred non-woven materials are provided from synthetic fibers, such as polyethylene, polyesters (particularly polyethylene terephthalate) and most preferably polypropylene. As the polymers used for nonwoven production are inherently hydrophobic, they are preferably coated with hydrophilic coatings, e.g., coated with nanoparticles, as known in the art.

In a preferred embodiment of the present invention the absorbent structure comprises: a wrapping material, the water-swellable material described herein, and a thermoplastic material and/or an adhesive and/or a thermoplastic adhesive, which may be a (non-absorbing) fibrous layer of adhesive.

Preferred absorbent structures can for example be made as follows:
a) providing a substrate material that can serve as a wrapping material;
b) depositing the water-swellable material herein onto a first surface of the substrate material, preferably in a pattern comprising at least one zone which is substantially free of water-swellable material, and the pattern comprising at least one zone comprising water-swellable material, preferably such that openings are formed between the separate zones with water-swellable material;
c) depositing a thermoplastic material onto the first surface of the substrate material and the water-swellable material, such that portions of the thermoplastic material are in direct contact with the first surface of the substrate and portions of the thermoplastic material are in direct contact with the water-swellable material;
d) and then typically closing the above by folding the substrate material over, or by placing another substrate matter over the above.

Preferred disposable absorbent article comprising the absorbent structure of the invention are sanitary napkins, panty liners, adult incontinence products and infant diapers or training or pull-on pants, whereby articles which serve to absorb urine, e.g., adult incontinence products, diapers and training or pull-on pants are the most preferred articles herein.

Preferred articles herein have a topsheet and a backsheet, which each have a front region, back region and crotch region, positioned therein between. The absorbent structure of the invention is typically positioned in between the topsheet and backsheet. Preferred backsheets are vapour pervious but liquid impervious. Preferred topsheet materials are at least partially hydrophilic; preferred are also so-called apertured topsheets. Preferred may be that the topsheet comprises a skin care composition, e.g., a lotion.

These preferred absorbent articles typically comprise a liquid impervious (but preferably air or water vapour pervious) backsheet, a fluid pervious topsheet joined to, or otherwise associated with the backsheet. Such articles are well known in the art and fully disclosed in various documents mentioned throughout the description.

Because the water-swellable material herein has a very high absorbency capacity, it is possible to use only low levels of this material in the absorbent articles herein. Preferred are thus thin absorbent articles, such as adult and infant diapers, training pants, sanitary napkins comprising an absorbent structure of the invention, the articles having an average caliper (thickness) in the crotch region of less than 1.0 cm, preferably less than 0.7 cm, more preferably less than 0.5 cm, or even less than 0.3 cm (for this purpose alone, the crotch region being defined as the central zone of the product, when laid out flat and stretched, having a dimension of 20% of the length of the article and 50% of the width of the article).

A preferred diaper herein has a front waist band and a back waist band, whereby the front waist band and back waist band each have a first end portion and a second end portion and a middle portion located between the end portions, and whereby preferably the end portions comprise each a fastening system, to fasten the front waist band to the rear waist band or whereby preferably the end portions are connected to one another, and whereby the middle portion of the back waist band and/or the back region of the backsheet and/or the crotch region of the backsheet comprises a landing member, preferably the landing member comprising second engaging elements selected from loops, hooks, slots, slits, buttons, magnets. Most preferred are hooks, adhesive or cohesive second engaging elements. Preferred may be that the engaging elements on the article, or preferably diaper are provided with a means to ensure they are only engage able at certain moments, for example, they may be covered by a removable tab, which is removed when the engaging elements are to be engaged and may be re-closed when engagement is no longer needed, as described above.

Preferred diapers and training pants herein have one or more sets of leg elastics and/or barrier leg cuffs, as known in the art.

Preferred may also be that the topsheet has an opening, preferably with elastication means along the length thereof, through which waste material can pass into a void space above the absorbent structure, and which ensures it is isolated in this void space, away from the wearer's skin.

Water-swellable Material

The water-swellable material herein is such that it swells in water by absorbing the water; it may thereby form a gel. It may also absorb other liquids and swell. Thus, when used herein, 'water-swellable' means that the material swells at least in water, but typically also in other liquids or solutions, preferably in water based liquids such as 0.9% saline.

The water-swellable material herein comprises water-swellable polymers that are coated with a coating agent, as described below. The water-swellable material may also contain water-swellable polymers that are not coated. However, the coated water-swellable polymers are preferably present at a level of at least 20% by weight (of the water-swellable material), more preferably from 50% to 100% by weight or even from 80% to 100% by weight, and most preferably between 90% and 100% by weight.

The coated water-swellable polymers may be present in the water-swellable material herein mixed with other components, such as fibers, (fibrous) glues, organic or inorganic filler materials or flowing aids, process aids, anti-caking agents, odor control agents, colouring agents, coatings to impart wet stickiness, hydrophilic surface coatings, etc.

The coating agent is applied such that the resulting coating layer is preferably thin; preferably the coating layer has an average caliper (thickness) between 1 micron (µm) and 100 microns, preferably from 1 micron to 50 microns, more preferably from 1 micron to 20 microns or even from 2 to 20 microns or even from 2 to 10 microns.

The coating is preferably uniform in caliper and/or shape. Preferably, the average caliper is such that the ratio of the smallest to largest caliper is from 1:1 to 1:5, preferably from 1:1 to 1:3, or even 1:1 to 1:2, or even 1:1 to 1:1.5.

The level of the coating agent is dependent on the level of the coated polymers, but typically, the coating agent is present at a level of 0.5% to 40% by weight of the water-swellable material, more preferably from 1% to 30% by weight or even from 1% to 20% by weight or even from 2% to 15% by weight.

The water-swellable material is typically obtainable by the process described herein, which is such that the resulting material is solid; this includes gels, flakes, fibers, agglomerates, large blocks, granules, particles, spheres and other forms known in the art for the water-swellable polymers described hereinafter.

Preferably, the material is in the form of particles having a mass median particle size between 10 microns up to 2 mm, or even between 50 microns and 1 mm, or preferably between 100 µm and 800 µm, as can for example be measured by the method set out in, for example, EP-A-0691133.

In one embodiment herein the water-swellable material herein is in the form of (free flowing) particles with particle sizes between 10 µm and 1200 µm or even between 50 µm and 800 µm and a mass median particle size between 100 and 800 µm or preferably even to 600 µm.

In addition, or in another embodiment herein, the water-swellable material comprises particles that are essentially spherical.

In yet another preferred embodiment herein the water-swellable material herein has a relatively narrow range of particle sizes with the majority (e.g., at least 80% or preferably at least 90% or even at least 95%) of particles having a particle size between 50 µm and 800 µm, preferably between 100 µm and 600 µm, and more preferably between 200 µm and 600 µm.

The water-swellable material herein preferably comprises less than 20% by weight of water, or even less than 10% or even less than 8% or even less than 5%, or even no water. The water-content of the water-swellable material can be determined by the EDANA test, number ERT 430.1-99 (February 1999) which involves drying the water-swellable material at 105° Celsius for 3 hours and determining the moisture content by the weight loss of the water-swellable materials after drying.

The water-swellable material herein is typically made such that it is in the form of so-called core-shell particles, whereby the water-swellable polymer(s) is present in the internal structure or core and the coating agent forms a coating shell around the water-swellable polymers, as described below in more detail.

In one preferred embodiment herein, the coating is an essentially continuous coating layer or shell around the water-swellable polymer (core), and said coating layer covers the entire surface of the polymer(s), i.e., no regions of the polymer's surface (core surface) are exposed. Hereby, it is believed that maximum tangential forces are exerted around the water-swellable polymer in the 'core' when the water-swellable material swells in a liquid, as described below. In particular in this embodiment, the coating materials and the resulting coatings are preferably highly water permeable such as to allow a fast penetration/absorption of liquid into the water-swellable material (into the core).

In another preferred embodiment herein, the coating shell or layer is porous, e.g., in the form of a network comprising pores for penetration of water, such as for example in the form of a fibrous network, e.g., that is connected and circumscribing the particle as defined herein.

In other words, it is highly preferred that the resulting coating or coating layer or shell, formed in the process herein, is pathwise connected and more preferably that the coating layer is pathwise connected and encapsulating (completely circumscribing) the water-swellable polymer(s) (see for example E. W. Weinstein et. al., Mathworld—A Wolfram Web Resource for 'encapsulation' and 'pathwise connected').

The coating layer is preferably a pathwise connected complete surface on the surface of the ('core' of the) water-swellable polymer(s). This complete surface consists of first areas where the coating agent is present and which are pathwise connected, e.g., like a network, and it may comprise second areas, where no coating agent is present, being for example micro pores, whereby said second areas are a disjoint union. Preferably, each second area, e.g., micropore, has a surface area of less than 0.1 mm$^2$, or even less than 0.01 mm$^2$ preferably less than 8000 µm$^2$, more preferably less than 2000 µm$^2$ and even more preferably less than 80 µm$^2$.

It is most preferred that no second areas are present, and that the coating agent forms a complete encapsulation around the water-swellable polymer (s).

Preferred may be that the water-swellable material comprises two or more layers of coating agent (shells), obtainable by coating the water-swellable polymers twice or more. This may be the same coating agent or a different coating agent.

Especially preferred water-swellable materials made by the process herein have a high sorption capacity measured by the Cylinder Centrifugation Retention Capacity, CCRC, test outlined below.

Especially preferred water-swellable materials made by the process herein have a high permeability for liquid such as can be measured by the SFC test disclosed in U.S. Pat. No. 5,599,335, U.S. Pat. No. 5,562,646 and U.S. Pat. No. 5,669,894 all of which are incorporated herein by reference.

Most preferred water-swellable materials made by the process herein have a high sorption capacity such as preferably measured by the CCRC test outlined below in combination with a high permeability (SFC) and high wet porosity (increased by the use of the coating agent).

In addition, especially preferred water-swellable materials made by the process herein have a high wet porosity (i.e., this means that once an amount of the water-swellable material herein is allowed to absorb a liquid and swell, it will typically form a (hydro)gel or (hydro)gel bed, which has a certain wet porosity, in particular compared to the uncoated water-swellable polymers, as can be measured by the SFC test set out herein (or with the PHL test disclosed in U.S. Pat. No.

5,562,646 which is incorporated herein by reference; if the water-swellable material and water-swellable polymers are to be tested at different pressures than described in the test method, the weight used in this test should be adjusted accordingly).

The use of the coating agent preferably increases the wet porosity of the water-swellable material herein, compared to the uncoated water-swellable polymers; preferably this increase is at least 50% or even at least 100%, or even at least 150%. More preferably, the wet porosity of the coated water-swellable materials herein increases under pressure such as the pressure caused by the wearer.

Water-swellable Polymers

The water-swellable polymers herein are preferably solid, preferably in the form of particles (which includes for example particles in the form of flakes, fibers, agglomerates); most preferably, the polymers are particles having a mass median particle size as specified above for the water-swellable material. The water-swellable polymers may have the mass median particle sizes and distributions as cited above for the coated materials, plus the thickness (caliper) of the coating; however, when for the purpose of the invention, the coating thickness is neglectable (for example being 2 to 20 microns), the water-swellable polymers typically have a mass median particle size/distribution which is the same as those cited above for the coated material.

As used herein, the term "water-swellable polymer" refers to a polymer which is substantially water-insoluble, water-swellable and preferably water-gelling, forming a hydrogel, and which has typically a Cylinder Centrifuge Retention Capacity (CCRC) as defined below of at least 10 g/g. These polymers are often also referred to in the art as (super-)absorbent polymers (SAP) or absorbent gelling materials (AGM).

These polymers are typically (lightly) crosslinked polymers, preferably lightly crosslinked hydrophilic polymers. While these polymers may in general be non-ionic, cationic, zwitterionic, or anionic, the preferred polymers are cationic or anionic. Especially preferred are acid polymers, which contain a multiplicity of acid functional groups such as carboxylic acid groups, or their salts, preferably sodium salts. Examples of acid polymers suitable for use herein include those which are prepared from polymerizable, acid-containing monomers, or monomers containing functional groups which can be converted to acid groups after polymerization. Such monomers include olefinically unsaturated carboxylic acids and anhydrides, and mixtures thereof. The acid polymers can also comprise polymers that are not prepared from olefinically unsaturated monomers. Examples of such polymers also include polysaccharide-based polymers such as carboxymethyl starch and carboxymethyl cellulose, and poly(amino acid) based polymers such as poly(aspartic acid). For a description of poly(amino acid) absorbent polymers, see, for example, U.S. Pat. No. 5,247,068, issued Sep. 21, 1993 to Donachy et al.

Some non-acid monomers can also be included, usually in minor amounts, in preparing the absorbent polymers herein. Such non-acid monomers can include, for example, monomers containing the following types of functional groups: carboxylate or sulfonate esters, hydroxyl groups, amide-groups, amino groups, nitrile groups, quaternary ammonium salt groups, and aryl groups (e.g., phenyl groups, such as those derived from styrene monomer). Other optional non-acid monomers include unsaturated hydrocarbons such as ethylene, propylene, 1-butene, butadiene, and isoprene.

These non-acid monomers are well-known materials and are described in greater detail, for example, in U.S. Pat. No. 4,076,663 (Masuda et al.), issued Feb. 28, 1978, and in U.S. Pat. No. 4,062,817 (Westerman), issued Dec. 13, 1977.

Olefinically unsaturated carboxylic acid and anhydride monomers useful herein include the acrylic acids typified by acrylic acid itself, methacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citroconic acid, mesaconic acid, glutaconic acid, aconitic acid, maleic acid, fumaric acid, tricarboxyethylene, and maleic anhydride.

Preferred water-swellable polymers contain carboxyl groups, such as the above-described carboxylic acid/carboxylate containing groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, hydrolyzed vinyl acetate-acrylic ester copolymers, hydrolyzed acrylonitrile or acrylamide copolymers, slightly network crosslinked polymers of any of the aforementioned copolymers, polyacrylic acid, and slightly network crosslinked polymers of polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Most preferred polymer materials used for making the water-swellable polymers herein are polyacrylates/acrylic acids and derivatives thereof, preferably (slightly) network crosslinked polymers partially neutralized polyacrylic acids and/or -starch derivatives thereof.

Preferred may be that partially neutralized polymeric acrylic acid is used in the process herein.

The water-swellable polymers useful herein can be formed by any polymerization and/or crosslinking techniques. Typical processes for producing these polymers are described in U.S. Reissue Pat. No. 32,649 (Brandt et al.), issued Apr. 19, 1988, U.S. Pat. No. 4,666,983 (Tsubakimoto et al.), issued May 19, 1987, and U.S. Pat. No. 4,625,001 (Tsubakimoto et al.), issued Nov. 25, 1986; U.S. Pat. No. 5,140,076 (Harada); U.S. Pat. No. 6,376,618 B1, U.S. Pat. No. 6,391,451 and U.S. Pat. No. 6,239,230 (Mitchell); U.S. Pat. No. 6,150,469 (Harada). Crosslinking can be affected during polymerization by incorporation of suitable crosslinking monomers. Alternatively, the polymers can be crosslinked after polymerization by reaction with a suitable reactive crosslinking agent. Surface crosslinking of the initially formed polymers is a preferred way to control to some extent the absorbent capacity, porosity and permeability.

The water-swellable polymers may also be surface-crosslinked, prior to, simultaneously with or after the coating step of the process herein. Suitable general methods for carrying out surface crosslinking of absorbent polymers according to the present invention are disclosed in U.S. Pat. No. 4,541,871 (Obayashi), issued Sep. 17, 1985; published PCT application WO92/16565 (Stanley), published Oct. 1, 1992, published PCT application WO90/08789 (Tai), published Aug. 9, 1990; published PCT application WO93/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308 (Makita), issued May 6, 1986; U.S. Pat. No. 4,734,478 (Tsubakimoto), issued Mar. 29, 1988; U.S. Pat. No. 5,164,459

(Kimura et al.), issued Nov. 17, 1992; published German patent application 4,020,780 (Dahmen), published Aug. 29, 1991;; U.S. Pat. No. 5,140,076 (Harada); U.S. Pat. No. 6,376,618 B1, U.S. Pat. No. 6,391,451 and U.S. Pat. No. 6,239,230 (Mitchell); U.S. Pat. No. 6,150,469 (Harada); and published European patent application 509,708 (Gartner), published Oct. 21, 1992.

Most preferably, the water-swellable polymers comprise from about 50% to 95% (mol percentage), preferably about 75 mol % neutralized, (slightly) crosslinked, polyacrylic acid (i.e., poly(sodium acrylate/acrylic acid)). Crosslinking renders the polymer substantially water-insoluble and, in part, determines the absorptive capacity and extractable polymer content characteristics of the absorbent polymers. Processes for crosslinking these polymers and typical bulk crosslinking agents are described in greater detail in U.S. Pat. No. 4,076,663.

While the water-swellable polymer is preferably of one type (i.e., homogeneous), mixtures of water-swellable polymers can also be used herein. For example, mixtures of starch-acrylic acid graft copolymers and slightly network crosslinked polymers of polyacrylic acid can be used herein. Mixtures of (coated) polymers with different physical properties, and optionally also different chemical properties, could also be used, e.g., different mean particle size, absorbent capacity, absorbent speed, SFC value, such as for example disclosed in U.S. Pat. No. 5,714,156 which is incorporated herein by reference.

The water-swellable polymers herein preferably have, prior to coating, a Cylinder Centrifuge Retention Capacity (CCRC) of at least 30 g/g, preferably at least 40 g/g, more preferably at least 50 g/g.

The water-swellable polymers preferably have a low amount of extractables, preferably less than 15% (by weight of the polymers), more preferably less than 10% and most preferably less than 5% of extractables, or even less than 3% (values of 1 hour test). The extractables and levels thereof and determination thereof are further described in for example U.S. Pat. No. 5,599,335; U.S. Pat. No. 5,562,646 or U.S. Pat. No. 5,669,894.

Coating Agent and Elastomeric Phase-separating Material Thereof

The coating agent herein comprises at least an elastomeric material that is phase-separating.

'Elastomeric' when used herein means that the material will exhibit stress induced deformation that is partially or completely reversed upon removal of the stress. The preferred tensile properties of elastomeric materials (formed into films) may be measured according to the test method defined herein to determine the wet and dry elongation to break and secant modulus at 400% elongation.

'Phase-separating' elastomeric material, when used herein, means that a film of the elastomeric material (i.e., prior to use in the coating agent and application to the water-swellable polymers) has at least two distinct spacial phases which are distinct and separated from one another, due to their thermodynamic incompatibility. The incompatible phases are comprised of aggregates of only one type of repeat unit or segment of the elastomeric material. This can for example occur when the elastomeric material is a block (or segmented) copolymer, or a blend of two immiscible polymers. The phenomenon of phase separation is for example described in: Thermoplastic Elastomers: A Comprehensive Review, eds. Legge, N. R., Holden, G., Schroeder, H. E., 1987, Chapter 2.

Typically, the phase separation occurs in a block copolymer, whereby the segment or block of the copolymer that has a Tg below room temperature (i.e., below 25° C.) is said to be the soft segment or soft block and the segment or block of the copolymer that has a Tg above room temperature is said to be the hard segment or hard block.

The Tg's, as referred to herein, may be measured by Differential Scanning Calorimetry (DSC) to measure the change in specific heat that a material undergoes upon heating. The DSC measures the energy required to maintain the temperature of a sample to be the same as the temperature of the inert reference material (e.g., Indium). A Tg is determined from the midpoint of the endothermic change in the slope of the baseline. The Tg values are reported from the second heating cycle so that any residual solvent in the sample is removed.

In addition, the phase separation can also be visualized by electron microscopy particularly if one phase can be stained preferentially. Also atomic force microscopy has been described as a particularly useful technique to characterize the morphology (phase-separating behavior) of the preferred thermoplastic polyurethanes, described herein after.

The elastomeric material herein comprises at least two phases with different glass transition temperatures (Tg); it comprises at least a first phase with a $Tg_1$, which is lower than the $Tg_2$ of a second phase, the difference being at least 30° C.

Preferably, the elastomeric material has a first (soft) phase with a $Tg_1$ which is less than 25° C., preferably less than 20° C., more preferably less than 0° C., or even less than −20° C., and a second (hard) phase with a $Tg_2$ of at least 50° C. or even at least 55° C., but more preferably more than 60° C. or even more than 70° C., or in certain embodiments, more than 100° C., provided the temperature difference between $Tg_1$ and $Tg_2$ is at least 30° C., preferably at least 50° C. or even at least 60° C., or in certain embodiments at least 90° C.

It should be understood that, for the purpose of the invention, the elastomeric material itself (i.e., before incorporation into the coating agent or before formation into the coating on the water-swellable polymers) has the herein specified properties, but that that typically, the elastomeric material maintains these properties once in the coating agent and/or in the coating, and that the resulting (film of the) coating should thus preferably have the same properties.

Typically, the elastomeric material and the coating agent need to be elastomeric in the wet state. Hence, the coating agent and/or the elastomeric material has (have) a wet-elongation at break of at least 400%, as determined by the test method described herein below (wherein a wet film of the elastomeric material or coating agent is submitted to specific conditions, in order to measure the wet-elongation at break; the elastomeric material is therefore thus a material that can be formed into a film, i.e., film-forming).

Preferably, the elastomeric material has a wet elongation at break of at least 400%, or even at least 500% or even at least 800% or even at least 1000%.

It should be understood for the purpose of the invention that a film or coating of the elastomeric material and the coating agent typically extend (in the wet state) their surface area, without (substantially) expanding in volume by liquid absorption. The elastomeric material and the coating agent are thus typically substantially non-water-swelling, as for example may be determined by the method set out herein below. This means in practice that the coating agent and/or the elastomeric material have preferably a water-swelling capacity of less than 1 g/g, or even less than 0.5 g/g, or even less than 0.2 g/g or even less than 0.1 g/g, as may be determined by the method, as set out below.

The inventors have found that (films of the) elastomeric materials with high moisture vapor transmission rates (at least 2100 g/m²/day as described by the method herein) have higher water or saline absorption than those with lower MVTR, however the water or saline absorption does not negatively affect the wet tensile properties of resulting coating.

The elastomeric material (and preferably the coating agent as a whole) has a tensile stress at break in the wet state of at least 1 MPa, or even at least 3 MPa and more preferably at least 5 MPa, or even at least 8 MPa. This can be determined by the wet tensile stress test method, described below.

Particularly preferred elastomeric materials and/or coating agents herein are materials that have a wet secant elastic modulus at 400% elongation ($SM_{wet\ 400\%}$) of at least 0.25 MPa, preferably at least about 0.50 MPa, more preferably at least about 0.75 MPa or even at least 2.0 MPa, and most preferably of at least about 3.0 MPa.

Preferred elastomeric materials or coating agents herein have a ratio of [wet secant elastic modulus at 400% elongation ($SM_{wet\ 400\%}$)] to [dry secant elastic modulus at 400% elongation ($SM_{dry\ 400\%}$)] of 1.4 or less, preferably 1.2 or less or even 1.0 or less, and it may be preferred that this ratio is at least 0.6, or even at least 0.7.

Preferably, the coating agent is present in the form of a coating that has a shell tension, which is defined as the (Theoretical equivalent shell caliper)×(Average wet secant elastic modulus at 400% elongation), of 2 to 20 N/m, or preferably 3 to 10 N/m, or more preferably 3 to 5 N/m.

The coating agent is preferably such that the resulting coating on the water-swellable polymers herein is water-permeable, but not water-soluble and, preferably not water-dispersible. The water permeability of the coating should be high enough such that the coated water-swellable material has a sufficiently high free swell rate as defined herein, preferably a free swell rate (FSR) of at least 0.05 g/g/sec, preferably at least 0.1 g/g/sec, and more preferably at least 0.2 g/g/sec.

The coating agent and/or the elastomeric material are preferably moderately or highly breathable, so that moisture vapour can pass. Preferably, the coating agent and/or elastomeric material (tested in the form of a film of a specific caliper, as described herein) is at least moderately breathable with a moisture vapour transmission rate (MVTR) of 800 g/m²/day or preferably 1200 g/m²/day to (inclusive) 1400 g/m²/day, preferably breathable with a MVTR of at least 1500 g/m²/day, up to 2000 g/m²/day (inclusive), and even more preferably that the coating agent or material is highly breathable with a MVTR of 2100 g/m²/day or more.

The elastomeric material may be a mixture of two or more different polymers that each has a different Tg, and which form a phase-separating mixture.

Preferred phase-separating elastomeric materials comprise a mixture of at least a (co)polymer selected of the following group A and a (co)polymer selected of the following group B:

A: poly ethylene (co) polymers, polypropylene (co) polymers, polybutylene (co) polymers, polyisoprene (co) polymers, polybutadiene (co) polymers, polyethylene-co-polypropylene, polyethylene-co-polybutylene, polyethylethylene-co-polypropylene, polyether (co) polymers, polyester (co) polymers; which all may optionally be grafted and/or be partially modified with chemical substituents (e.g., hydroxyl groups or carboxylates);

B: polyvinyl (co) polymers (e.g., styrene, vinylacetate, vinylformamide), polyurethanes (co) polymers, polyester (co) polymers, polyamide (co) polymers, polydimethylsiloxanes, proteins; which all may optionally be grafted and/or be partially modified with chemical substituents (e.g., hydroxyl groups or carboxylates).

More preferably, the elastomeric material comprises one or more phase-separating block copolymer(s), whereby each of the block copolymers has two or more Tg's. Especially preferred phase-separating elastomeric materials herein comprise one or more phase-separating block copolymer, having a weight average molecular weight Mw of at least 50 kDa, preferably at least 70 kDa.

Such a block copolymer has at least a first polymerized homopolymer segment (block) and a second polymerized homopolymer segment (block), polymerized with one another, whereby preferably the first (soft) segment has a $Tg_1$ of less than 25° C. or even less than 20° C., or even less than 0° C., and the second (hard) segment has a $Tg_2$ of at least 50° C., or of 55° C. or more, preferably 60° C. or more or even 70° C. or more.

The total weight average molecular weight of the hard second segments (with a Tg of at least 50° C.), is preferably at least 28 kDa, or even at least 45 kDa.

The preferred weight average molecular weight of a first (soft) segment is at least 500 Da, preferably at least 1000 Da or even at least 2000 Da, but preferably less than 8000 Da, preferably less than 5000 Da.

However, the total of the total of the first (soft) segments is typically 20% to 95% by weight of the total block copolymer, or even from 20% to 70% or more preferably from 30% to 60% or even from 30% to 40% by weight. Furthermore, when the total weight level of soft segments is more than 70%, it is even more preferred that an individual soft segment has a weight average molecular weight of less than 5000 Da.

It may be preferred that the block copolymer comprises a mixture of different soft segments and/or a mixture of different hard segments, for example a mixture of different soft segments that each have a different Tg, but all less than 25° C. or even less than 20° C., or even less than 0° C., or for example a mixture of hard segments, each having a different Tg, but all greater than 50° C.

The precise weight level (in the block copolymer) of the first segments that have a Tg of less than 25° C., or even less than 20° C. or even less than 0° C., will depend on the required tensile strength of the resulting coating, e.g., by decreasing the weight level of the first segments in the block copolymer, the tensile strength may increase. However, when the weight percentage of the first segments is too low, the MVTR may be lower than desirable.

The block copolymers useful herein are preferably block copolymers that have intermolecular H-bonding.

The block copolymers useful herein are preferably selected from: polyurethane (co) polyethers, polyurethane (co)polyesters, polyurethane/urea- co-polyethers or -co (poly)esters, polystyrene block copolymers, hydrogenated polystyrene block copolymers, polyester (co) polyethers, polyester (co) polyethers, polyamide- co-polyethers or -co (poly)esters, polyoxyethylene-co-polyepichlorohydrin.

Preferred are polyurethane-co- poly(ethylene glycol), polyurethane-co-poly(tetramethylene glycol), and polyurethane-co- poly(propylene glycol) and mixtures thereof.

The polyurethane (hard) segments are preferably derived from a polymerisation reaction of a diisocyanate with a diol, such as for example butane diol, or cyclohexane diol, or preferably from a polymerisation reaction of an aromatic diisocyanate and an aliphatic diol such as ethylene glycol, butane diol, propane diol, or mixtures thereof.

A preferred diisocyanate used to form the polyurethane segments of the block copolymers herein is methylene bis (phenyl isocyanate).

The hard segments are reacted with for example macrodiols to form the preferred phase-separated block copolymers herein.

Preferred may be that the elastomeric phase-separating material comprises a block copolymer with poly(tetramethylene glycol), or more preferably poly(ethylene glycol) segments (as first (soft) segments with a Tg of less than 20° C.), because poly(ethylene glycol) provides a higher breathability of the resulting coating. Also, the molecular weight percentage (by weight of the total block copolymer; as discussed above) of these first (soft) segments can be selected to provide the required breathability, e.g., a higher percentage of these segments will provide a more breathable coating.

Preferred phase-separating block copolymers are Vector 4211, Vector 4111, Septon 2063, Septon 2007, Estane 58245, Estane 4988, Estane 4986, Estane T5410, Irogran PS370-201, Irogran VP 654/5, Pellethane 2103-70A, Elastollan LP 9109. Estane is a trade name of Noveon Inc., 9911 Brecksville Road, Cleveland, Ohio 44141-3247, USA. Vector is a trade name of Dexco Polymers, 12012 Wickchester Lane, Houston, Tex. 77079, USA, Septon is a trade name of the Septon Company of America, A Kuraray Group Company, 11414 Choate Road, Pasadena, Tex. 77507, USA, Irogran is a trade name of Huntsman Polyurethanes, 52 Kendall Pond Road, Derry, N.H. 03038, USA, Pellethane is a trade name of the Dow Chemical Company, 2040 Dow Center, Midland, Mich. 48674, USA and Elastollan is a trade name of BASF, 1609 Biddle Avenue, Wyandotte, Mich. 48192.

If may be preferred that the coating agent herein comprises fillers to reduce tack such as the commercially available resin Estane 58245-047P, available from Noveon Inc., 9911 Brecksville Road, Cleveland, Ohio 44141-3247, USA; or the commercially available films Duraflex PT1700S, Duraflex PT1710S, Duraflex U073, Duraflex X2075, available from Deerfield Urethane, P.O. Box 186, South Deerfield, Mass. 01373.

Preferred polymeric elastomeric materials for use in the coating agent herein are strain hardening and/or strain crystallizing. Strain Hardening occurs after the rubbery plateau and is the rapid increase in stress with increasing strain. Strain hardening can introduce orientation in the film producing greater resistance to extension in the direction of drawing.

While there are some elastomeric polymers that are strain crystallizing, this property can also be imparted by the addition or blending of additional materials into the coating agent or polymer, such as organic or inorganic fillers. Nonlimiting examples of inorganic fillers include various water-insoluble salts, and other (preferably nanoparticulate) materials such as for example chemically modified silica, also called active or semi-active silica that are for example available as fillers for synthetic rubbers. Examples for such fillers are UltraSil VN3, UltraSil VN3P, UltraSil VN2P, and UltraSil 7000GR available from Degussa AG, Weißfrauenstraße 9, D-60287 Frankfurt am Main, Germany.

Preferred fillers are organic or inorganic compounds which are useful as flow agents in the processes described herein, and which typically reduce the stickiness of the coated water-swellable materials or the water-swellable polymers to be coated. Examples of such flow aids are semi-active or hydrophobic silica, urea formaldehyde, (sodium) silicates, diatomaceous earth and clays.

The coating agent and/or the elastomeric material are preferably hydrophilic and in particular surface hydrophilic. The surface hydrophilicity may be determined by methods known to those skilled in the art. In a preferred execution, the hydrophilic coating agents or elastomeric materials are materials that are wetted by the liquid that is to be absorbed (0.9% saline; urine). They may be characterized by a contact angle that is less than 90 degrees. Contact angles can for example be measured with the Video-based contact angle measurement device, Krüss G10-G1041, available from Kruess, Germany or by other methods known in the art.

It may also be preferred that the resulting water-swellable material is hydrophilic. The hydrophilicity of water-swellable materials may be measured as described in co-pending application EP03014926.4

If the elastomeric material or the coating agent itself is not hydrophilic, the coating agent can be made hydrophilic for example by treating it with surfactants, plasma coating, plasma polymerization, or other hydrophilic surface treatments as known to those skilled in the art.

Preferred compounds to be added to make the hydrophilic coating agent, or subsequently added to the resulting coated water-swellable polymers are for example: N-(2-Acetamido)-2-aminoethansulfonic-acid, N-(2-Acetamido)-imino-di-acetic-acid, N-acetyl-glycine, β-Alanine, Aluminum-hydroxy-acetate, N-Amidino-glycine, 2-Amino-ethyl-hydrogenphosphate, 2-Amino-ethyl-hydrogensulfate, Amino-methan-sulfonic acid, Maleinic acid, Arginine, Asparaginic acid, Butane-diacid, Bis(1-aminoguanidinium)-sulfate, 2-Oxo-propionic acid, Tri-Calcium-dicitrate, Calcium gluconate, Calcium saccharate, Calcium-Titriplex®, Carnitin, Cellobiose, Citrullin, Creatine, Dimethylaminoacetic acid, THAM-1,2-disulfonic-acid, Ethylendiammonium sulfate, Fructose, Fumaric acid, Galactose, Glucosamine, Gluconic-acid, Glutamine, 2-Amino-glutaric-acid, Glutaric acid, Glycine, Glycylglycine, Iminodiacetic acid, Magnesium glycerophosphate, Oxalic acid, Tetrahydroxy-adipinic acid, Taurin, N-Methyl-taurin, Tris-(hydroxymethyl)-aminomethane, N-(Tris-(hydroxymethyl)-methyl)-2-aminoethansulfonic acid.

Alternatively, the coating agent can be made hydrophilic with a hydrophilicity boosting composition comprising a hydrophilicity-boosting amount of nanoparticles. By hydrophilicity boosting amount, it is intended that an amount of nanoparticles be present in the hydrophilicity boosting compositions, which are sufficient to make a substrate to which it is applied more hydrophilic. Such amounts are readily ascertained by one of ordinary skill in the art; it is based on many factors, including but not limited to, the substrate used, the nanoparticles used, the desired hydrophilicity of the resulting water-swellable material.

Nanoparticles are particles that have a primary particle size, that is diameter, which is in the order of magnitude of nanometers. That is, nanoparticles have a particle size ranging from about 1 to about 750 nanometers. Nanoparticles with particle sizes ranging from about 2 nm to about 750 nm can be economically produced. Non-limiting examples of particle size distributions of the nanoparticles are those that fall within the range from about 2 nm to less than about 750 nm, alternatively from about 2 nm to less than about 200 nm, and alternatively from about 2 nm to less than about 150 nm.

The particle size of the nanoparticles is the largest diameter of a nanoparticle and may be measured by any methods known to those skilled in the art.

The mean particle size of various types of nanoparticles (as determined from the nanoparticle size distribution) may differ from the individual particle size of the nanoparticles particles. For example, a layered synthetic silicate can have a mean particle size of about 25 nanometers while its particle size distribution can generally vary between about 10 nm to about 40 nm. (It should be understood that the particle sizes that are described herein are for particles when they are dispersed in an aqueous medium and the mean particle size is based on the mean of the particle number distribution. Non-limiting examples of nanoparticles can include crystalline or amorphous particles with a particle size from about 2 to about 750 nanometers. Boehmite alumina can have an average particle size distribution from 2 to 750 nm.

The hydrophilicity boosting composition may consist of the nanoparticles, and then the nanoparticles are directly added to the surface-treatment agent or to the process, e.g., in step b).

Alternatively, the nanoparticles are present in a composition with other carrier ingredients, e.g., solvents or disperent liquids; in one preferred embodiment the nanoparticles are applied in step b) as a dispersion in a liquid. If the hydrophilicity boosting composition does not consist of the nanoparticles, but comprises other ingredients, then it is preferred that the nanoparticles are present in the hydrophilicity boosting compositions at levels of from about 0.0001% to about 50%, preferably from about 0.001% to about 20% or even to 15%, and more preferably from about 0.001% to about 10%, by weight of the composition.

Either organic or inorganic nanoparticles may be used in the hydrophilicity boosting composition; inorganic nanoparticles are preferred. Inorganic nanoparticles generally exist as oxides, silicates, carbonates and hydroxides. Some layered clay minerals and inorganic metal oxides can be examples of nanoparticles. The layered clay minerals suitable for use herein include those in the geological classes of the smectites, the kaolins, the illites, the chlorites, the attapulgites and the mixed layer clays. Typical examples of specific clays belonging to these classes are the smectices, kaolins, illites, chlorites, attapulgites and mixed layer clays. Smectites, for example, include montmorillonite, bentonite, pyrophyllite, hectorite, saponite, sauconite, nontronite, talc, beidellite, volchonskoite. Kaolins include kaolinite, dickite, nacrite, antigorite, anauxite, halloysite, indellite and chrysotile. Illites include bravaisite, muscovite, paragonite, phlogopite and biotite, and vermiculite. Chlorites include corrensite, penninite, donbassite, sudoite, pennine and clinochlore. Attapulgites include sepiolite and polygorskyte. Mixed layer clays include allevardite and vermiculitebiotite. Variants and isomorphic substitutions of these layered clay minerals offer unique applications.

Layered clay minerals may be either naturally occurring or synthetic. An example of one non-limiting embodiment of the coating composition uses natural or synthetic hectorites, montmorillonites and bentonites. Another embodiment uses the hectorites clays commercially available, and typical sources of commercial hectorites are the LAPONITEs™ from Southern Clay Products, Inc., U.S.A; VEEGUM Pro and VEEGUM F from R. T. Vanderbilt, U.S.A.; and the Barasyms, Macaloids and Propaloids from Baroid Division, National Read Comp., U.S.A.

In one preferred embodiment herein the nanoparticles comprise a synthetic hectorite a lithium magnesium silicate. One such suitable lithium magnesium silicate is LAPONITE™, which has the formula:

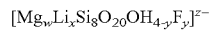

$$[Mg_wLi_xSi_8O_{20}OH_{4-y}F_y]^{z-}$$

wherein w=3 to 6, x=0 to 3, y=0 to 4, z=12−2w−x, and the overall negative lattice charge is balanced by counter-ions; and wherein the counter-ions are selected from the group consisting of selected $Na^+$, $K^+$, $NH_4^+$, $Cs^+$, $Li^+$, $Mg^{++}$, $Ca^{++}$, $Ba^{++}$, $N(CH_3)_4^+$ and mixtures thereof. (If the LAPONITE™ is "modified" with a cationic organic compound, then the "counter-ion" could be viewed as being any cationic organic group ($R^+$).)

Other suitable synthetic hectorites include, but are not limited to isomorphous substitutions of LAPONITE™, such as, LAPONITE B™, LAPONITE S™, LAPONITE XLS™, LAPONITE RD™, LAPONITE XLG™, and LAPONITE RDS™.

The nanoparticles may also be other inorganic materials, including inorganic oxides such as, but not limited to, titanium oxide silica, zirconium oxide, aluminum oxide, magnesium oxide and combinations thereof. Other suitable inorganic oxides include various other inorganic oxides of alumina and silica.

In one preferred embodiment herein the nanoparticles comprise a Boehmite alumina ($[Al(O)(OH)]_n$) which is a water dispersible, inorganic metal oxide that can be prepared to have a variety of particle sizes or range of particle sizes, including a mean particle size distribution from about 2 nm to less than or equal to about 750 nm. For example, a boehmite alumina nanoparticle with a mean particle size distribution of around 25 nm under the trade name Disperal P2™ and a nanoparticle with a mean particle size distribution of around 140 nm under the trade name of Dispal® 14N4-25 are available from North American Sasol, Inc.

In one preferred embodiment herein the nanoparticles are selected from the group consisting of titanium dioxide, Boehmite alumina, sodium magnesium lithium fluorosilicates and combinations thereof.

Use of mixtures of nanoparticles in the hydrophilicity boosting compositions is also within the scope of the present invention.

Optionally, in addition to or in place of water, the carrier can comprise a low molecular weight organic solvent. Preferably, the solvent is highly soluble in water, e.g., ethanol, methanol, acetone, methyl ethyl ketone, dimethylformamide, ethylene glycol, propanol, isopropanol, and the like, and mixtures thereof. Low molecular weight alcohols can reduce the surface tension of the nanoparticle dispersion to improve wettability of the substrate. This is particularly helpful when the substrate is hydrophobic. Low molecular weight alcohols can also help the treated substrate to dry faster. The optional water-soluble low molecular weight solvent can be used at any suitable level. The carrier can comprise any suitable amount of the composition, including but not limited to from about 10% to about 99%, alternatively from about 30% to about 95%, by weight of the coating composition.

The hydrophilicity boosting composition may also comprise organic, e.g., latex nanoparticles, so-called nanolatexes. A "nanolatex", as used herein, is a latex with a particle size less than or equal to about 750 nm. A "latex" is a dispersion of water-insoluble polymer particles that are usually spherical in shape. Nanolatexes may be formed by emulsion polymerization. "Emulsion polymerization" is a process in which monomers of the latex are dispersed in water using a surfactant to form a stable emulsion followed by polymerization. Particles are typically produced which can range in size from about 2 nm to about 600 nm. When the nanolatexes are elastomeric material, e.g., film-forming elastomeric polymers, then they are considered coating agents for the purpose of the invention, and not (part of) a hydrophilicity boosting composition.

Surfactants are especially useful as additional ingredient of the coating agent herein, or as additional ingredients in the process step a) or b) herein, e.g., as wetting agents to facilitate the dispersion of the coating agent onto the substrate. Surfactants are preferably included when the coating composition is used to treat a hydrophobic substrate.

Suitable surfactants can be selected from the group including anionic surfactants, cationic surfactants, nonionic surfactants, amphoteric surfactants, ampholytic surfactants, zwitterionic surfactants and mixtures thereof. Nonlimiting examples of surfactants useful in the compositions herein are disclosed in McCutcheon's, Detergents and Emulsifiers, North American edition (1986), published by Allured Publishing Corporation; McCutcheon's, Functional Materials, North American Edition (1992); U.S. Pat. Nos. 5,707,950 and 5,576,282; and U.S. Pat. No. 3,929,678, to Laughlin et al., issued Dec. 30, 1975.

When a surfactant is used in the coating composition, it may be added at an effective amount to provide or facilitate application of the coating composition. Surfactant, when present, is typically employed in compositions at levels of from about 0.0001% to about 60%, preferably from about 0.001% to about 35%, and more preferably from about 0.001% to about 25%, by weight of the composition.

Nonlimiting examples of surfactants, including preferred nonionic surfactants, useful herein typically at levels from about 0.001% to about 60%, by weight, include nonionic and amphoteric surfactants such as the $C_{12}$-$C_{18}$ alkyl ethoxylates ("AE") including the so-called narrow peaked alkyl ethoxylates and $C_6$-$C_{12}$ alkyl phenol alkoxylates (especially ethoxylates and mixed ethoxy/propoxy), $C_{12}$—$C_{18}$ betaines and sulfobetaines ("sultaines"), $C_{10}$-$C_{18}$ amine oxides, and the like. Another class of useful surfactants is silicone surfactants and/or silicones. They can be used alone and/or alternatively in combination with the alkyl ethoxylate surfactants described herein. Nonlimiting examples of silicone surfactants are the polyalkylene oxide polysiloxanes having a dimethyl polysiloxane hydrophobic moiety and one or more hydrophilic polyalkylene side chains, and having the general formula:

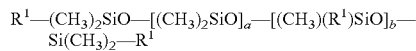

$$R^1\text{—}(CH_3)_2SiO\text{—}[(CH_3)_2SiO]_a\text{—}[(CH_3)(R^1)SiO]_b\text{—}Si(CH_3)_2\text{—}R^1$$

wherein a+b are from about 1 to about 50, and each $R^1$ is the same or different and is selected from the group consisting of methyl and a poly(ethyleneoxide/propyleneoxide) copolymer group having the general formula: —$(CH_2)_n O(C_2H_4^\circ)_c (C_3H_6^\circ)_d R^2$, wherein n is 3 or 4; total c (for all polyalkyleneoxy side groups) has a value of from 1 to about 100, alternatively from about 6 to about 100; total d is from 0 to about 14; alternatively d is 0; total c+d has a value of from about 5 to about 150, alternatively from about 9 to about 100 and each $R^2$ is the same or different and is selected from the group consisting of hydrogen, an alkyl having 1 to 4 carbon atoms, and an acetyl group, alternatively hydrogen and methyl group. Each polyalkylene oxide polysiloxane has at least one $R^1$ group being a poly(ethyleneoxide/propyleneoxide) copolymer group. Silicone superwetting agents are available from Dow Corning as silicone glycol copolymers (e.g., Q2-5211 and Q2-5212).

It is also within the scope of the present invention to use a mixture of surfactants.

The coating agent may be applied in fluid form, e.g., as a melt (or so-called hotmelt), solution or dispersion. Thus, the coating agent may also comprise a solvent or dispersing liquid, such as water, THF (tetrahydrofuran), methylethyl ketone, dimethylformamide, toluene, dichloromethane, cyclohexane or other solvents or dispersing liquids that are able to dissolve or disperse the elastomeric material (e.g., elastomeric polymer) and subsequently can be evaporated such as to form a (dry) coating shell or layer.

Preferably, the coating agent comprises from 0% to 95% by weight of a dispersing liquid or solvent, such as water. Preferred is that the coating agent comprises at least 5% by weight (of the coating agent) of the elastomeric material, more preferably from 10% to 80% or even from 20% to 70%, the remaining percentage being said liquid and/or fillers/hydrophilicity aids, spreading aids etc, as described herein.

The inventors also found that the process of applying and subsequently treating the coating agent may be important in order to impart high elongation in the wet state.

While some elastomeric materials may already have high wet elongation per se, it may be useful to apply an annealing step, as described herein, to the material.

In addition to providing the right mechanical properties in the wet state as it is outlined above, preferred coating agents herein preferably also have other desired properties such as high resistance against mechanical abrasion in order to survive processing into absorbent articles or structures, without significant deterioration of their properties. They also are preferably colorless, or white and opaque and may in addition contain other materials such for example to control odor, release perfumes, and the like.

Preferred Process Herein for Making the Solid Water-swellable Material

The water-swellable material is preferably obtainable by a process comprising the steps of:

a) obtaining water-swellable polymer particles;

b) simultaneously with or subsequently to step a), applying a coating agent to at least a part of said water-swellable polymers particles, and optionally the step of c) annealing the resulting coated water-swellable polymer particles of step b), to obtain the water-swellable material herein, whereby said coating agent of step b) is as described herein.

In step a) 'obtaining' the water-swellable polymer particles, as described herein above, includes using commercially available water-swellable polymer particles, or forming the water-swellable polymer particles by any known process from precursors.

The coating step b) may be done by any known method, for example by mixing or dispersing the water-swellable polymers (or precursors thereto) in the coating agent or (hot) melt or solution or dispersion thereof; by spraying the coating agent, or said (hot) melt, solution or dispersion thereof onto the polymers; by introducing the coating agent, or melt, dispersion or solution thereof, and the water-swellable polymers (or precursors thereto) in a fluidised bed or Wurster coater; by agglomerating the coating agent, or melt, solution or dispersion thereof, and the water-swellable polymers (or precursors thereof); by dip-coating the (particulate) water-swellable polymers in the coating agent, melt, dispersion or solution thereof. Other suitable mixers include for example twin drum mixers, so called "Zig-Zag" mixers, plough-share mixers, such as Lödige mixers, cone screw mixers, or perpendicularly cylindrical mixers having coaxially rotating blades. Examples of preferred coating processes are for example described in U.S. Pat. No. 5,840,329 and U.S. Pat. No. 6,387,495.

In an alternative embodiment herein, the coating step b) may be done by applying the coating agent in the form of a foam, preferably in the form of an open-cell foam, leading to a porous coating. In yet an alternative embodiment the coating step may be done by forming a fibrous network on the surface of the water-swellable material such as for example by applying the coating agent in the form of meltblown microfibers, such that an essentially connected coating is formed (as described herein).

To apply the coating agent, it may also comprise solvents such as water and/or organic, optionally water-miscible, solvents. Suitable organic solvents are, for example, aliphatic and aromatic hydrocarbons, alcohols, ethers, esters, amides and ketones. Suitable water-miscible solvents are, for example, aliphatic alcohols, polyhydric alcohols, ethers, amides and ketones.

If the coating agent is in the form of a solution or dispersion, it may be further preferred to add processing aids, subsequently or prior to the coating step b), e.g., in order to aid a good film formation of the coating layer.

In the optional step c), the resulting coated water-swellable polymers are annealed. The optional annealing step c) typically involves a step resulting in a further strengthened or more continuous or more completely connected coating and it may eliminate defects.

Typically, the annealing step) involves a heat treatment of the resulting coated water-swellable polymers; it may be done by for example radiation heating, oven heating, convection heating, azeotropic heating, and it may for example take place in conventional equipment used for drying, such as fluidized bed driers. Preferred may be that a vacuum is applied as well or that the annealing is done under an inert gas (to avoid oxidation).

Preferably, the annealing step involves heating the coated water-swellable polymers at a temperature which is above the highest Tg of the coating agent or the elastomeric phase-separating material thereof, preferably to a temperature which is at least 20° C. above said highest Tg.

For example, the highest Tg is typically at least 50° C. and the annealing temperature is at least 70° C., or even at least 100° C. or even at least 140° C., and up to 200° C. or even up to 250° C.

If the material has a melting temperature Tm, then the annealing step is at least 20° C. below the Tm and if possible and preferably at least 20° C. or even at least 50° C. above the highest Tg.

The annealing step may be done for, for example, at least 5 minutes, or even for at least 10 minutes or even for at least 15 minutes, or even at least 30 minutes or even at least 1 hour or even at least 2 hours.

This heat-treatment may be done once, or it may be repeated, for example, the heat treatment may be repeated with different temperatures, for example first at a lower temperature, for example from 70° C. or 80° C., to 100° C., as described above, for example, for at least 30 minutes or even 1 hour, up to 12 hours, and subsequently at a higher temperature, for example, from 120° C. to 140° C., for at least 10 minutes.

Typically, the temperature and time are adjusted in order to allow good coating (film) formation and good phase-separation, such as to form mechanically strong coatings (films).

During the annealing step, the coated water-swellable polymers may also be dried at the same time. Alternatively, a separate drying step may take place.

The resulting water-swellable material is preferably solid and thus, if the water-swellable polymers of step a) or the resulting coated polymers of step b) are not solid, a subsequent process step is required to solidify the resulting coated polymers of step b), e.g., a so-called solidifying or preferably particle forming step, as known in the art. This may be done prior to, or simultaneously with step c).

The solidifying step includes for example drying the water-swellable polymers and/or the coated polymers of step b) (e.g., if the step b involve a dispersion or solution of any of the ingredients) by increasing the temperature and/or applying a vacuum, as described herein. This may be done simultaneously with, or occur automatically with the annealing step c). The solidifying step may also include a cooling step, if for example a melt is used.

Subsequently, any known particle forming process may also be used here for, including agglomeration, extrusion, grinding and optionally followed by sieving to obtain the required particle size distribution.

The inventors found another preferred way to provide elastomeric coatings on cores of water-swellable polymers, namely by providing a coating that has a significantly larger surface area than the outer surface area of the water-swellable polymer (core), so that when the polymers swell, the coating can 'unfold' and extend. The inventors found a very easy and convenient way to provide such coated water-swellable polymers, namely by applying the coating agent on water-swellable polymers, which are in swollen state due to absorption of a liquid (e.g., water), and then removing the liquid or part thereof, so that the water-swellable polymers (in the core) shrink again, but the coating maintains its original surface area. The surface area of the coating is then larger than the surface area of the polymer core, and the coating is then typically wrinkled; it can unwrinkle when the water-swellable polymers absorb water and swell, without encountering any strain/stress on the coating due to the swelling of the water-swellable polymers. Thus, the coating agent is wet-extensible or elastomeric, without much exposure to strain or stress and without the risk of rupturing.

A highly preferred process thus involves the step of obtaining water-swellable polymers (particles) and immersing these in a dispersion or solution of an elastomeric material in a liquid that may comprise an amount of water to swell the water-swellable polymers, typically under thorough stirring.

The water-swellable polymers may absorb the liquid, and thereby, the elastomeric material is automatically 'transferred' to the surface of water-swellable polymers (particles). The amount of water-swellable polymers and amount of liquid, including water, and elastomeric material can be adjusted such that the water-swellable polymers can absorb about all water present in the solution or dispersion and that when this is achieved, the water-swellable polymers, coated with elastomeric material, are in the form of gel "particles". The resulting coating is typically under zero strain/stress.

The process may also involve addition of further processing aids in any of the steps, such as granulation aids, flow aids, drying aids. For some types of coating agents, the coated water-swellable polymers may potentially form agglomerates. Any flow aids known in the art may be added (for example, prior to or during the coating step, or preferably during the drying and/or annealing step, as discussed below; for example Aerosil 200, available from Degussa has been found to be a good flow aid).

Highly preferred may be that the process involves addition of a spreading aid and/or surfactant, as described above, which facilitates the coating step b).

Process Examples and Materials Made by the Process

Preparation of Water-swellable Polymers that are Especially Useful for Use in Process Step a) Herein.

EXAMPLE 1.1

Process for Preparation of Spherical Water-swellable Polymer Particles

Spherical core polymer particles may be obtained UMSICHT (Fraunhofer Institut Umwelt- Sicherheits-, Energietechnik, Oberhausen, Germany), or made by following the adapted procedure below:

40 g glacial acrylic acid (AA) is placed into a beaker, and 1712 mg MethyleneBisAcrylAmide (MBAA) is dissolved in the acid. Separately, 13.224 g solid NaOH is dissolved in 58.228 g water and cooled. The NaOH solution is then slowly added to the acrylic acid, and the resulting solution is chilled to 4-10° C.

In a second beaker, 400 mg ammoniumperoxodisulfate (APS) and 400 mg sodiummetabisulfite are mixed and dissolved in 99.2 ml water. This solution is also chilled to 4-10° C.

With the use of two equal peristaltic pumps, both solutions are combined and pumped at equal rates through a short static mixer unit, after which they are dropped as individual droplets into 60-80° C. hot silicone oil (Roth M 50, cat. # 4212.2) which is in a heated, about 2 m long, glass tube. The pump rate is adjusted such that individual droplets sink through the oil in the tube, while also avoiding premature polymerization in the mixer unit. The polymerization proceeds during the descent of the droplets through the oil, and particles (gelled polymer droplets) are formed, which can be collected in a heated 1 liter Erlenmeyer flask attached to the bottom of the tube.

After completion of the addition, the oil is allowed to cool, and the spheres are collected by draining the oil. Excess oil is removed by washing with i-propanol, and the particles (spheres) are pre-dried by exposing them to excess i-propanol for 12-24 hours. Additional washings with i-propanol may be needed to remove traces of the silicone oil. The particles (spheres) are then dried in a vacuum oven at 60-100° C. until a constant weight is obtained.

The amount of MBAA may be adjusted, depending on what properties are required from the resulting polymers, e.g., when 0.3 mol % (per mol AA) MBAA is used, the resulting water-swellable polymer particles have a CCRC of about 50 g/g (absorption of 0.9% saline solution, as determined by methods known in the art and described herein); when 1.0 mol % (per mol AA) MBAA is used, the resulting water-swellable polymer particles have a CCRC of about 19 g/g; when 2.0 mol % (per mol AA) MBAA is used, the resulting water-swellable polymer particles have a CCRC of about 9 g/g.

All compounds were obtained by Aldrich Chemicals, and used without further purification.

EXAMPLE 1.2

Process for the Preparation of Water-swellable Polymers Useful Herein

To 300 g of glacial acrylic acid (AA), an appropriate amount of the core crosslinker (e.g., MethyleneBisAcrylAmide, MBAA) is added (see above) and allowed to dissolve at ambient temperature. A 2500 ml resin kettle (equipped with a four-necked glass cover closed with septa, suited for the introduction of a thermometer, syringe needles, and optionally a mechanical stirrer) is charged with this acrylic acid/crosslinker solution. Typically, a magnetic stirrer, capable of mixing the whole content, is added. An amount of water is calculated so that the total weight of all ingredients for the polymerization equals 1500 g (i.e., the concentration of AA is 20 w/w-%). 300 mg of the initiator ("V50" from Waco Chemicals) are dissolved in approx. 20 ml of this calculated amount of deionized water. Most of the water is added to the resin kettle, and the mixture is stirred until the monomer and water are well mixed. Then, the initiator solution is added together with any remaining water. The resin kettle is closed, and a pressure relief is provided e.g., by puncturing two syringe needles through the septa. The solution is then spurged vigorously with argon via an 80 cm injection needle while stirring at ~300 RPM. Stirring is discontinued after ~8 minutes, while argon spurging is continued. The solution typically starts to gel after 12-20 minutes total. At this point, persistent bubbles form on the surface of the gel, and the argon injection needle is raised above the surface of the gel. Purging with argon is continued at a lowered flow rate. The temperature is monitored, typically it rises from 20° C. to 60-70° C. within an hour. Once the temperature drops below 60° C., the kettle is transferred into a circulation oven and kept at 60° C. for 15-18 hours.

After this time, the resin kettle is allowed to cool, and the resulting gel is removed into a flat glass dish. The gel is then broken or cut with scissors into small pieces (for example, in pieces smaller than 2 mm max. dimension), and transferred into a 6 liter glass beaker. The amount of NaOH (50%) needed to neutralize 75% of the acid groups of the polymer is diluted with deionized water to 2.5 liters, and added quickly to the gel. The gel is stirred until all the liquid is absorbed; then, it is covered and transferred into a 60° C. oven and let equilibrate for 2 days.

After this time, the gel is allowed to cool, then divided up into 2 flat glass dishes, and transferred into a vacuum oven, where it is dried at 100° C./max. vacuum. Once the gel has reached a constant weight (usually 3 days), it is ground using a mechanical mill (e.g., IKA mill) and sieved to obtain water-swellable polymer particles of the required particle size, e.g., 150-800 µm.

(At this point, key parameters of the water-swellable polymer as used herein may be determined).

The amount of MBAA may be adjusted, depending on what properties are required from the resulting polymers, e.g., when 0.01 mol % (per mol AA) MBAA is used, the resulting water-swellable polymer particles have a CCRC of about 90 g/g (absorption of 0.9% saline solution, as determined by methods known in the art and described herein); when 0.03 mol % (per mol AA) MBAA is used, the resulting water-swellable polymer particles have a CCRC of about 73 g/g; when 0.1 mol % (per mol AA) MBAA is used, the resulting water-swellable polymer particles have a CCRC of about 56 g/g; when 2.0 mol % (per mol AA) MBAA is used, the resulting water-swellable polymer particles have a CCRC of about 16 g/g; when 5.0 mol % (per mol AA) MBAA is used, the resulting water-swellable polymer particles have a CCRC of about 8 g/g.

(All compounds were obtained by Aldrich Chemicals, and used without purification.)

EXAMPLE 1.3

Surface Cross-linking Process Step

This example demonstrates surface crosslinking of water-swellable polymers prior to subjecting them to the process step b) herein. A 150 ml glass beaker is equipped with a mechanical stirrer with a plastic blade, and charged with 4 g of a dry water-swellable polymer in particulate form. The mechanical stirrer is selected in such a way that a good fluidization of the polymers can be obtained at 300-500 RPM. A 50-200 µl syringe is charged with a 4% solution (w/w) of DENACOL (=Ethylene Glycol DiGlycidyl Ether=EGDGE) in 1,2-propanediol; another 300 µl syringe is charged with deionised water.

The water-swellable polymers are fluidized in the beaker at approx. 300 RPM, and the surface cross-linking agent is added within 30 seconds. Mixing is continued for a total of three minutes. While stirring is continued, 300 µl of water are then added within 3-5 seconds, and stirring is continued at 300-500 RPM for another 3 minutes. After this time, the mixture is transferred into a glass vial, sealed with aluminum foil, and let equilibrate for 1 hour. Then the vial is transferred to a 140° C. oven, and kept at this temperature for 120 minutes. After this time, the vial is allowed to cool, the contents are removed, and the surface cross-linked water-swellable polymer is obtained. Any agglomerates may be carefully broken by gentle mechanical action. The resulting surface cross-linked water-swellable polymer particles may then be sieved to the desired particle size.

The Following Examples Show Coating Processes that are Used to Demonstrate the Coatings Step b) of the Preferred Processes Described Herein.

EXAMPLE 2.1

Process of Providing Coated Water-swellable Materials by Directly Mixing Them into a Water Based Dispersion of the Elastomeric Phase-separating Polymer The following is a preferred process for making the water-swellable material herein, involving swelling the water-swellable polymers prior to, or simultaneously with the coating step. The amount of water-swellable polymers to be coated, coating level and water needed to swell the water-swellable polymers is chosen.

Then, the dispersion or solution of the coating agent or elastomeric material is prepared by mixing a commercial available coating agent or elastomeric material and water with optionally THF under stirring, for example in a glass beaker using magnetic stirrers at about 300 rpm for about 5 minutes. At all times, care needs to be taken that no film is formed on the surface of the dispersion. Typically such dispersion contains at the most 70% by weight of elastomeric polymer.

In order to monitor the coating process better, a staining color might be added to the dispersion, for example New Fuchsin Red.

Then, a mechanical stirrer with a double cross Teflon blade is used and the dispersion is stirred such that a vortex can be seen, and then the water-swellable polymer (particles) are quickly added under continuous stirring. Once the water-swellable polymers start absorbing the water from the dispersion (typically after about 15 seconds), the mixture will start to gel and the vortex will eventually disappear. Then, when about all of the free liquid has been absorbed, the stirring is stopped and the resulting coated water-swellable polymers may be dried or post treated by any of the methods described herein.

EXAMPLE 2.2

Process of Providing Coated Water-swellable Materials by Directly Mixing Them into an Elastomer Solution The following is a preferred process for making the water-swellable material herein, involving swelling the water-swellable polymers prior to, or simultaneously with the coating step.

The amount of water-swellable polymers to be coated, coating level and water needed to swell the water-swellable polymers is chosen.

Then, the solution of the coating agent is prepared, by dissolving the commercial available coating agent, such as Estane 58245 in an organic solvent (e.g., THF or a mixture of water and THF, if required), for example in a glass beaker for 1 hour to 24 hours.

In order to monitor the coating process better, a staining color might be added to the dispersion, for example, New Fuchsin Red.

Then, this solution is added to the water-swellable polymer that is being stirred or mechanically agitated to provide the coating. When the free liquid has been absorbed into the water-swellable polymer, the stirring is stopped and the resulting coated water-swellable polymers may be dried or post treated by any of the methods described herein.

EXAMPLE 2.3

Process of Providing Individually Coated Water-swellable Materials

An alternative preferred coating process herein is as follows:

The (solid, particulate) water-swellable polymers are placed on a surface that is preferably under an angle (30-45 degrees).

The coating agent, in the form of a solution, is applied in drops, e.g., by use of a pipette or by spraying, onto the polymers. Hereby, no air bubbles should be formed.

Thus, a film is formed on the surface of the water-swellable polymers.

These coated water-swellable polymers are then dried, either at room temperature (20° C.), or for example at 40° C./80% humidity, for up to 2 days, or for example in an oven (if required, a vacuum oven) at a low temperature (up to 70° C.).

The coated water-swellable material can then be annealed as described below.

It may then also be formed into the desired form, e.g., particles.

EXAMPLE 2.4

Alternative Preferred Coating Process

In another preferred process, a dispersion of the water-swellable polymers is prepared first and the coating agent is added thereto.

For example, 200 grams of a water-swellable polymer (cross-linked polyacrylic acid based polymers, for example prepared by the method described above) is placed in a plastic beaker and n-heptane is added, until the heptane stands about 1-2 mm above the surface of the polymers in the beaker; this is typically about 100 g of n-heptane.

Using a household mixer (e.g., for whipping cream), the components are mixed at high speed. The coating agent, in the form of a solution of an elastomeric coating material, e.g., a polyurethane solution as described above, is added to the beaker with the water-swellable polymers by use of for example a pipette. The mixture is continuously stirred, avoiding the formation of lumps.

The resulting material can be spread out over a surface as a thin layer (e.g., less than 1 cm) and allowed to air dry for at least 12 hours or in a (vacuum) oven (any temperature up to about 70° C.

After cooling or subsequent steps, the resulting material may be mechanically reduced or sieved to the desired particle sizes.

EXAMPLE 2.5

Process of Providing Coated Water-swellable Materials using a Fluidized Bed Wurster Coater Step b) may also be done in a fluidized bed or Wurster coater.

For example, a Lakso Wurster Model 101 (The Lakso Company, Leominster, Mass.) may be used or a Glatt GPCG-3 granulator-coater may be used (supplied by Glatt Ingenieurtechnik GmbH, Nordstrasse 12, 99427 Weimar, Germany). It may be desired that the coating equipment is pre-heated, for example to 70° C., under air flow, for example for about 30 minutes.

For example, typically between 20 and 35 g of water-swellable polymer is placed in the vessel.

The coating agent, preferably in fluid form, such as the polymer solutions/dispersions listed below, is placed in a container on the stirring platform and stirred using a magnetic bar at low speed to prevent entrainment of air. The weight can be recorded.

The peristaltic pump is calibrated and then set to the desired flow rate (e.g., 5 g/minute) and the direction of flow of the coating agent is set forward. The desired inlet air flow and temperature are set to 50 $m^3$/hr and 60° C. Then, the 'atomizing' air supply and pump are started. The outlet temperature of the system is maintained at 45° C. by adjusting the solvent flow rate into the system.

(A higher speed may be used to advance the coating agent closer towards the inlet of the coater and then setting the correct speed for the experiment.)

The experiment is typically complete when stickiness prevents efficient fluidization of the powder (between 10 and 60 minutes).

Then, the coating agent flow is stopped immediately and flow reversed. The weight of coating agent used in the experiment is recorded.

Optionally, the resulting coated water-swellable polymers may be dried within the coater, which also may aid to reduce particle surface stickiness (drying time typically between 5 and 60 minutes).

Then, the material inside the coater is weighed.

In general, the material may be returned to the coating vessel to continue the process, if required, e.g., if more than one coating agent is to be applied or to add a flow aid, e.g., 0.5-2% hydrophobic silica.

In general, a filler may be added (e.g., to the solution) to reduce tackiness of the coated water-swellable material, for example 1-5% by weight of a filler with a median particle size of less 5 microns, to make thin coatings with an average caliper of for example 5 microns to 20 microns or even to 10 microns In order to visualise the coating process, or for aesthetic purposes, a colouring agent or dye solution may be added to the coating agent, for example New Fuchsin Red (0.25 g of New Fuchsin Red in 5 ml to 25 ml deionised water (15-25° C.), without entrainment of air bubbles). The dye solution can be added drop-wise to about 10 ml of the coating agent under stirring and this can then be stirred into the remaining coating agent (sufficient for up to 70 ml coating agent).

The following water-swellable materials have been made by the process above, using a fluid bed coater or Wurster coater; in each case, 500 g of the uncoated water-swellable polymers, available as ASAP 500 from BASF, have been used and the specified amount of polymer, at the specified weight-% solids concentration, have been used.

The coated samples were dried under vacuum for 24 h at room temperature.

| Example | Polymer | Polymer Concentration (% w/w) | Solvent | Amount of Polymer (% w/w) |
|---|---|---|---|---|
| 1 | Vector 4211 | 10 | MEK | 2.8 |
| 2 | Vector 4211 | 12 | MEK | 5.5 |
| 3 | Irogran 654/5 | 5 | MEK | 1.4 |
| 4 | Irogran 654/5 | 5 | MEK | 1.6 |
| 5 | Septon 2063 | 10 | Toluene | 6.7 |
| 6 | Estane 58245 | 5 | DMF | 1.4 |

Vector is a trade name of Dexco Polymers, 12012 Wickchester Lane, Houston, Tex. 77079, USA; Irogran is a trade name of Huntsman Polyurethanes, 52 Kendall Pond Road, Derry, N.H. 03038, USA; Septon is a trade name of the Septon Company of America, A Kuraray Group Company, 11414 Choate Road, Pasadena, Tex. 77507, USA; Estane is a trade name of Noveon Inc., 9911 Brecksville Road, Cleveland, Ohio 44141-3247, USA.

EXAMPLE 2.6

Preferred Subsequent Process Steps of Drying and/or Annealing

The process herein may comprise a step whereby a solution, suspension or dispersion or solution is used, e.g., whereby the water-swellable polymers comprise a liquid (water) or whereby the coating agent is in the form of a dispersion, suspension or solution.

The following is a preferred process step of drying the coated water-swellable polymers of step b):

The coated water-swellable material comprising a liquid, e.g., water, is placed on a surface, for example, it is spread out in a Pyrex glass pan in the form of a layer which is not more than about 1 cm thick. This is dried at about 50 Celsius for at least 12 hours.

If the amount of liquid present in the coated water-swellable polymers is known, then, by measuring the coated water-swellable material comprising said weight of liquid prior to drying and then subsequently after drying, one can determine the residual moisture in the resulting water-swellable material (coated water-swellable polymers) as known in the art. Typically, the resulting water-swellable material/coated water-swellable polymers will be dried to less than 5% (by weight of the material) moisture content.

The coated water-swellable polymers or material may subsequently be annealed, as described herein.

For some type of coating agents, coated water-swellable polymers may potentially form agglomerates. Flow aids may be added prior to or during the coating step, or preferably during the drying and/or annealing step as known in the art, e.g., Aerosil 200, available from Degussa.

The above drying step may also be done by spreading the coated water-swellable polymers on a Teflon coated mesh in a very thin layer, e.g., less than 5 mm, such as to enable convection through the layer.

As alternative method, the coated water-swellable polymers that contain a liquid (water), may also be directly dried and annealed in one step, e.g., placing the material in a vacuum oven at 120 or 140 Celsius for 2 hours, or at a temperature that is appropriate for the polymer that is used as determined by the thermal transitions that occur for that polymer.

EXAMPLE 2.7

Example: Method of Drying in Fluidized Bed

A Lakso Wuster coater as used in example 2.5 and other fluidized bed driers known in the art may also be used to dry the coated materials formed by step b) of the process. For example, the conditions of example 2.5 might be used, introducing the coated material (and thus using the Wurster coating equipment only for drying the coated material).

EXAMPLE 2.8

Method of Azeotropic Distillation and Drying

The wet, coated polymers may be dried or dewatered at low-temperature via azeotropic distillation from a suitable liquid, which does not dissolve the coating agent, for example cyclohexane, provided the coating agent does not dissolve in cyclohexane. For example, the coated polymers are transferred to a 2 liter resin kettle, equipped with a Trubore mechanical stirrer with Teflon blade and digital stirring motor, immersion thermometer, and Barrett type moisture receiver with graduated sidearm and water-cooled condenser. Approximately one liter of cyclohexane is added to the resin kettle. While stirring, a heating mantle is used to raise the temperature of the stirred cyclohexane/gel system to reflux. Reflux is continued until the temperature of the system approaches the boiling point of cyclohexane (approximately 80° C.) and only minimal additional quantity of water is delivered to the sidearm. The system is cooled and then filtered to obtain the dewatered or dried coated water-swellable polymers, which may be further dried overnight under vacuum at ambient temperature (20° C.).

Test Methods Used Herein:

Preparation of Films of the Coating Agent

In order to subject the coating agents or phase-separating elastomeric material used herein to some of the test methods below, including the Wet-elongation test, films need to be obtained of said coating agents or phase separating elastomeric material thereof.

The preferred average (as set out below) caliper of the (dry) films for evaluation in the test methods herein is around 60 µm.

Methods to prepare films are generally known to those skilled in the art and typically comprise solvent casting, hot melt extrusion or melt blowing films. Films prepared by these methods may have a machine direction that is defined as the direction the film is drawn or pulled. The direction perpendicular to the machine direction is defined as the cross-direction.

For the purpose of the invention, the films used in the test methods below are formed by solvent casting, except when the coating agent or phase-separating material cannot be made into a solution or dispersion of any of the solvents listed below, and then the films are made by hotmelt extrusion as described below. (The latter is the case when particulate matter from the phase-separating material is still visible in the mixture of the material or coating agent and the solvent, after attempting to dissolve or disperse it at room temperature for a period between 2 to 48 hours, or when the viscosity of the solution or dispersion is too high to allow film casting.)

It should be understood that in the first embodiment herein, when an annealing step is only optional, the films are prepared without the annealing step. If the annealing step is required, then the films to be tested are made by a process below, involving an annealing step as well.

The resulting film should have a smooth surface and be free of visible defects such as air bubbles or cracks.

An Example to Prepare a Solvent Cast Film Herein from a Phase-separating Elastomeric Material or Coating Agent:

The film to be subjected to the tests herein can be prepared by casting a film from a solution or dispersion of said material or coating agent as follows:

The solution or dispersion is prepared by dissolving or dispersing the phase-separating material or coating agent, at 10 weight %, in water, or if this is not possible, in THF (tetrahydrofuran), or if this is not possible, in dimethylformamide (DMF), or if this is not possible in methyl ethyl ketone (MEK), or if this is not possible, in dichloromethane or if this is not possible in toluene, or if this is not possible in cyclohexane (and if this is not possible, the hotmelt extrusion process below is used to form a film).

Next, the dispersion or solution is poured into a Teflon boat with aluminum foil to slow evaporation, and the solvent or dispersant is slowly evaporated at a temperature above the minimum film forming temperature of the polymer, typically about 25° C., for a long period of time, e.g., during at least 48 hours, or even up to 7 days. Then, the films are placed in a vacuum oven for 6 hours, at 25° C., to ensure any remaining solvent is removed.

The Process to Prepare a Hotmelt Extruded Film Herein is as Follows:

If the solvent casting method is not possible, films of the coating agent or phase-separating material herein may be extruded from a hot melt using a rotating single screw extrusion set of equipment operating at temperatures sufficiently high to allow the material or coating agent to flow. If the material or coating agent has a melting temperature Tm, then the extrusion should takes place at least 20° C. above said Tm. If the material or coating agent is amorphous (i.e., does not have a Tm), steady shear viscometry can be performed to determine the order to disorder transition for the material, or the temperature where the viscosity drops dramatically. The direction that the film is drawn from the extruder is defined as the machine direction and the direction perpendicular to the drawing direction is defined as the cross direction.

| For example | Wet-extensible material | Die Temperature | Screw rpm |
|---|---|---|---|
| 8 | Irogran VP 654/5 | 180° C. | 40 |
| 8 | Elastollan LP 9109 | 170° C. | 30 |
| 9 | Estane 58245 | 180° C. | 30 |
| 10 | Estane 4988 | 180° C. | 30 |
| 11 | Pellethane 2103-70A | 185° C. | 30 |

Annealing of the Films:

If the process herein involves an annealing step, and if the water-swellable material herein comprises an annealed coating, then the films used in the test method are annealed. This annealing of the films (prepared and dried as set out above) should, for the purpose of the test methods below, be done by placing the film in a vacuum oven at a temperature which is about 20° C. above the highest Tg of the used coating agent or used phase-separating elastomeric material, and this is done for 2 hours in a vacuum oven at less than 0.1 Torr, provided that when the coating agent or elastomeric material has a melting temperature Tm, the annealing temperature is at least 20° C. below the Tm, and then preferably (as close to) 20° C. above the highest Tg. When the Tg is reached, the temperature should be increased slowly above the highest Tg to avoid gaseous discharge that may lead to bubbles in the film. For example, a material with a hard segment Tg of 70° C. might be annealed at 90° C. for 10 min, followed by incremental increases in temperature until the annealing temperature is reached.

If the coating agent or phase-separating material has a Ti, then said annealing of the films (prepared as set out above and to be tested by the methods below) is done at a temperature which is above the (highest) Tg and at least 20° C. below the Tm and (as close to) 20° C. above the (highest) Tg. For example, a wet-extensible material that has a Tm of 135° C. and a highest Tg (of the hard segment) of 100° C., would be annealed at 115° C.

Removal of Films, if Applicable

If the dried and optionally annealed films are difficult to remove from the film forming substrate, then they may be placed in a warm water bath for 30 s to 1 min to remove the films from the substrate. The film is then subsequently dried for 6-24 h at 25° C.

Wet-elongation Test and Wet-tensile-stress Test:

This test method is used to measure the wet-elongation at break (=extensibility at break) and tensile properties of films of phase-separating material or coating agents as used herein, by applying a uniaxial strain to a flat sample and measuring the force that is required to elongate the sample. The film samples are herein strained in the cross-direction, when applicable.

A preferred piece of equipment to do the tests is a tensile tester such as a MTS Synergie100 or a MTS Alliance available from MTS Systems Corporation 14000 Technology Drive, Eden Prairie, Minn., USA, with a 25N or 50N load cell. This measures the Constant Rate of Extension in which the pulling grip moves at a uniform rate and the force measuring mechanisms moves a negligible distance (less than 0.13 mm) with increasing force. The load cell is selected such that the measured loads (e.g., force) of the tested samples will be between 10 and 90% of the capacity of the load cell.

Each sample is die-cut from a film, each sample being 1×1 inch (2.5×2.5 cm), as defined above, using an anvil hydraulic press die to cut the film into sample(s) (Thus, when the film is made by a process that does not introduce any orientation, the film may be tested in either direction.). Test specimens (minimum of three) are chosen which are substantially free of visible defects such as air bubbles, holes, inclusions, and cuts. They must also have sharp and substantially defect-free edges.

The thickness of each dry specimen is measured to an accuracy of 0.001 mm with a low pressure caliper gauge such as a Mitutoyo Caliper Gauge using a pressure of about 0.7 kPa. Three different areas of the sample are measured and the average caliper is determined. The dry weight of each specimen is measured using a standard analytical balance to an accuracy of 0.001 g and recorded. Dry specimens are tested without further preparation for the determination of dry-elongation, dry-secant modulus, and dry-tensile stress values used herein.

For wet testing, pre-weighed dry film specimens are immersed in saline solution [0.9% (w/w) NaCl] for a period of 24 hours at ambient temperature (23°+/−2° C.). Films are secured in the bath with a 120-mesh corrosion-resistant metal screen that prevents the sample from rolling up and sticking to itself. The film is removed from the bath and blotted dry with an absorbent tissue such as a Bounty™ towel, to remove excess or non-absorbed solution from the surface. The wet caliper is determined as noted for the dry samples. Wet specimens are used for tensile testing without further preparation. Testing should be completed within 5 minutes after preparation is completed. Wet specimens are evaluated to determine wet-elongation, wet-secant modulus, and wet-tensile stress.

For the purpose of the present invention the Elongation to (or at) Break will be called Wet-elongation to (or at) Break and the tensile stress at break will be called Wet Stress at Break. (At the moment of break, the elongation to break % is the wet extensibility at break as used herein.)

Tensile testing is performed on a constant rate of extension tensile tester with computer interface such as an MTS Alliance tensile tester with Testworks 4 software. Load cells are selected such that measured forces fall within 10-90% of the cell capacity. Pneumatic jaws, fitted with flat 2.54 cm-square rubber-faced grips, are set to give a gage length of 2.54 cm. The specimen is loaded with sufficient tension to eliminate observable slack, but less than 0.05N. The specimens are extended at a constant crosshead speed of 25.4 cm/min until the specimen completely breaks. If the specimen breaks at the grip interface or slippage within the grips is detected, then the data is disregarded and the test is repeated with a new specimen and the grip pressure is appropriately adjusted. Samples are run in triplicate to account for film variability.

The resulting tensile force-displacement data are converted to stress-strain curves using the initial sample dimensions from which the elongation, tensile stress, and modulus that are used herein are derived. Tensile stress at break is defined as the maximum stress measured as a specimen is taken to break, and is reported in MPa. The break point is defined as the point on the stress-strain curve at which the measured stress falls to 90% of its maximum value. The elongation at break is defined as the strain at that break point and is reported relative to the initial gauge length as a percentage. The secant modulus at 400% elongation is defined as the slope of the line that intersects the stress-strain curve at 0% and 400% strain. Three stress-strain curves are generated for each extensible film coating that is evaluated. Elongation, tensile stress, and modulus used herein are the average of the respective values derived from each curve.

The dry secant elastic modulus at 400% elongation ($SM_{dry, 400\%}$) is calculated by submitting a dry film, as obtainable by the methods described above (but without soaking it in the 0.9% NaCl solution), to the same tensile test described above, and then calculating the slope of the line intersecting with the zero intercept and the stress-strain curve at 400%, as done above.

Glass Transition Temperatures

Glass Transition Temperatures (Tg's) are determined for the purpose of this invention by differential scanning calorimetry (DSC). The calorimeter should be capable of heating/cooling rates of at least 20° C./min over a temperature range, which includes the expected Tg's of the sample that is to be tested, e.g., of from −90° to 250° C., and the calorimeter should have a sensitivity of about 0.2 μW. TA Instruments Q1000 DSC is well-suited to determining the Tg's referred to herein. The material of interest can be analyzed using a temperature program such as: equilibrate at −90° C., ramp at 20° C./min to 120° C., hold isothermal for 5 minutes, ramp 20° C./min to −90° C., hold isothermal for 5 minutes, ramp 20° C./min to 250° C. The data (heat flow versus temperature) from the second heat cycle is used to calculate the Tg via a standard half extrapolated heat capacity temperature algo rithm. Typically, 3-5 mg of a sample material is weighed (+/−0.1 mg) into an aluminum DSC pan with crimped lid.

As used herein $Tg_1$ will be a lower temperature than $Tg_2$.

Polymer Molecular Weights

Gel Permeation Chromatography with Multi-Angle Light Scattering Detection (GPC-MALS) may be used for determining the molecular weight of the phase-separating polymers herein. Molecular weights referred to herein are the weight-average molar mass (Mw). A suitable system for making these measurements consists of a DAWN DSP Laser Photometer (Wyatt Technology), an Optilab DSP Interferometric Refractometer (Wyatt Technology), and a standard HPLC pump, such as a Waters 600E system, all run via ASTRA software (Wyatt Technology).

As with any chromatographic separation, the choice of solvent, column, temperature and elution profiles and conditions depends upon the specific polymer which is to be tested. The following conditions have been found to be generally applicable for the phase-separating polymers referred to herein: Tetrahydrofuran (THF) is used as solvent and mobile phase; a flow rate of 1 mL/min is passed through two 300×7.5 mm, 5 μm, PLgel, Mixed-C GPC columns (Polymer Labs) which are placed in series and are heated to 40-45° C. (the Optilab refractometer is held at the same temperature); 100 μL of a 0.2% polymer solution in THF solution is injected for analysis. The dn/dc values are obtained from the literature where available or calculated with ASTRA utility. The weight-average molar mass (Mw) is calculated by with the ASTRA software using the Zimm fit method.

Moisture Vapor Transmission Rate Method (MVTR Method)

MVTR method measures the amount of water vapor that is transmitted through a film under specific temperature and humidity. The transmitted vapor is absorbed by $CaCl_2$ desiccant and determined gravimetrically. Samples are evaluated in triplicate, along with a reference film sample of established permeability (e.g., Exxon Exxaire microporous material #XBF-110W) that is used as a positive control.

This test uses a flanged cup (machined from Delrin (McMaster-Carr Catalog #8572K34) and anhydrous $CaCl_2$ (Wako Pure Chemical Industries, Richmond, Va.; Catalog 030-00525). The height of the cup is 55 mm with an inner diameter of 30 mm and an outer diameter of 45 mm. The cup is fitted with a silicone gasket and lid containing 3 holes for thumb screws to completely seal the cup. Desiccant particles are of a size to pass through a No. 8 sieve but not through a No. 10 sieve. Film specimens approximately 3.8 cm×6.4 cm that are free of obvious defects are used for the analysis. The film must completely cover the cup opening, A, which is 0.0007065 $m^2$.

The cup is filled with $CaCl_2$ to within 1 cm of the top. The cup is tapped on the counter 10 times, and the $CaCl_2$ surface is leveled. The amount of $CaCl_2$ is adjusted until the headspace between the film surface and the top of the $CaCl_2$ is 1.0 cm. The film is placed on top of the cup across the opening (30 mm) and is secured using the silicone gasket, retaining ring, and thumb screws. Properly installed, the specimen should not be wrinkled or stretched. The sample assembly is weighed with an analytical balance and recorded to ±0.001 g. The assembly is placed in a constant temperature (40±3° C.) and humidity (75±3% RH) chamber for 5.0 hr±5 min. The sample assembly is removed, covered with Saran Wrap® and is secured with a rubber band. The sample is equilibrated to room temperature for 30 min, the plastic wrap removed, and the assembly is reweighed and the weight is recorded to ±0.001 g. The absorbed moisture $M_a$ is the difference in initial and final assembly weights. MVTR, in $g/m^2/24$ hr ($g/m^2/$day), is calculated as:

$$MVTR = M_a/(A*0.208 \text{ day})$$

Replicate results are averaged and rounded to the nearest 100 $g/m^2/24$ hr, e.g., 2865 $g/m^2/24$ hr is herein given as 2900 $g/m^2/24$ hr and 275 $g/m^2/24$ hr is given as 300 $g/m^2/24$ hr.

Method of Determining the Water Swellability Capacity of Wet-Extensible Materials used Herein, Considered Non-water-swellable The elastomeric material herein is non-water swelling and/or absorbing, which means that it absorbs typically less than 1 g water/g material, or even less than 0.5 g/g or even less than 0.2 g/g or even less than 0.1 g/g.

The water absorption can be determined as follows.

A certain, pre-weighed amount of the elastomeric material (sample), with weight M (sample), is immersed in an excess amount of deionized water and is allowed to 'absorb' water for about 2.5 hours.

The sample is gently removed from the water; if possible, excess water is blotted from the sample with tissue towel for few seconds. The sample is then weighed again and the wet sample weight M (sample-wet) is determined.

The water absorption capacity of the sample, X (AC sample), is determined by the following formula:

$$X(\text{AC sample}) = \{M(\text{sample wet}) - M(\text{sample})\}/M(\text{sample})$$

The value X is reported in gram of absorbed fluid per gram of dry film sample.

The water absorption as determined is herein also called Water Swellability (or Swelling) Capacity of the phase-separating elastomeric material.

Cylinder Centrifuge Retention Capacity

The Cylinder Centrifuge Retention Capacity (CCRC) method determines the fluid retention capacity of the water-swellable materials or polymers (sample) after centrifugation at an acceleration of 250 g. Prior to centrifugation, the sample is allowed to swell in excess saline solution in a rigid sample cylinder with mesh bottom and an open top.

This method is particularly applicable to materials having fluid retention capacities that are substantially higher than 40 g/g and consequently not well-suited to evaluation by tea bag methods (e.g., EDANA 441.2-02, U.S. Pat. No. 6,359,192 B1, U.S. Pat. No. 5,415,643). Duplicate sample specimens are evaluated for each material tested and the average value is reported.

The CCRC can be measured at ambient temperature by placing the sample material (1.0+/−0.001 g) into a pre-weighed (+/−0.01 g) Plexiglas sample container that is open at the top and closed on the bottom with a stainless steel mesh (400) that readily allows for saline flow into the cylinder but contains the absorbent particles being evaluated. The sample cylinder approximates a rectangular prism with rounded-edges in the 67 mm height dimension. The base dimensions (78×58 mm OD, 67.2×47.2 MM ID) precisely match those of modular tube adapters, herein referred to as the cylinder stand, which fit into the rectangular rotor buckets (Heraeus # 75002252, VWR # 20300-084) of the centrifuge (Heraeus Megafuge 1.0; Heraeus # 75003491, VWR # 20300-016).

The loaded sample cylinders are gently shaken to evenly distribute the sample across the mesh surface and then placed upright in a pan containing saline solution. The cylinders should be positioned to ensure free flow of saline through the mesh bottom. Cylinders should not be placed against each other or against the wall of the pan, or sealed against the pan bottom. The sample is allowed to swell, without confining pressure and in excess saline, for a time that corresponds to 80% of the CCRC saturation or equilibrium time for the specific material under study. The saturation time is determined from a plot of CCRC values versus increasing swell time (60 minute increments). As used here, saturation time is defined as the swell time required to reach the saturation/equilibrium CCRC value. The saturation value is determined by sequentially calculating the standard deviation (SD) of the CCRC values of three consecutive points on the curve (the first SD calculated corresponds to time points 1-3, the second SD to time points 2-4, the third SD to time points 3-5, and so on). The saturation value is defined as the largest of the three consecutive CCRC values having a standard deviation of less than 2.

Cylinders are immediately removed from the solution. Each cylinder is placed (mesh side down) onto a cylinder stand and the resulting assembly is loaded into the rotor basket such that the two sample assemblies are in balancing positions in the centrifuge rotor.

The samples are centrifuged for 3 minutes (±10 s) after achieving the rotor velocity required to generate a centrifugal acceleration of 250±5 g at the bottom of the cylinder stand. The openings in the cylinder stands allow any solution expelled from the absorbent by the applied centrifugal forces to flow from the sample to the bottom of the rotor bucket where it is contained. The sample cylinders are promptly removed after the rotor comes to rest and weighed to the nearest 0.01 g.

The cylinder centrifuge retention capacity expressed as grams of saline solution absorbed per gram of sample material (e.g., water-swellable material) is calculated for each replicate as follows:

$$CCRC = \frac{m_{CS} - (m_{Cb} + m_S)}{m_S} \left[\frac{g}{g}\right]$$

where:

$m_{CS}$: is the mass of the cylinder with sample after centrifugation [g]

$m_{Cb}$: is the mass of the dry cylinder without sample [g]

$m_S$: is the mass of the sample without saline solution [g]

The CCRC referred to herein is the average of the duplicate samples reported to the nearest 0.01 g/g.

Saline Flow Conductivity (SFC)

A measure of permeability and an indication of porosity is provided by the saline flow conductivity of the gel bed as described in U.S. Pat. No. 5,562,646, (Goldman et al.) issued Oct. 8, 1996 (whereby however a 0.9% NaCl solution is used instead of Jayco solution).

Extractables or Extractable Polymers Value

Another important characteristic of particularly preferred water-swellable materials and the water-swellable polymers useful herein is the level of extractable polymer material or extractables present therein. Evaluation and explanation of which levels of extractable polymer is still acceptable is disclosed and explained in detail in U.S. Pat. No. 4,654,039. As a general rule the extractable amount should be as low as possible and the lower it is the less undesired reaction the extractable material can cause. Preferred are levels of extractables of less than 10% by weight, or even less than 5% or even less than 3% (1 hour test values).

Method to Determine the Free Swell Rate of Water-swellable Materials Herein

This method serves to determine the swell rate of the water-swellable materials herein in a 0.9% saline solution, without stirring or confining pressure. The amount of time taken to absorb a certain amount of fluid is recorded and this is reported in gram of fluid (0.9% saline) absorbed per gram of water-swellable material per second, e.g., g/g/sec.

The saline solution is prepared by adding 9.0 gram of NaCl into 1000 ml distilled, deionized water, and this is stirred until all NaCl is dissolved.

The sample material (1.0 g+/−0.001 g) is weighed and placed evenly over the bottom of a 25 ml beaker. A 20.0 ml aliquot of the saline solution (also at 23° C.) is promptly poured into the beaker. A timer is started immediately after the saline solution is delivered and stopped when the final portion of the fluid phase coalesces with the swelling sample.

This is readily indicated by the loss of light reflection from the bulk saline surface, particularly at the interface with the beaker walls. The elapsed time, $t_s$, in seconds is recorded. The free swell rate, in g liquid/g sample material/sec, is calculated as: $FSR=20/t_s$. The test is run in triplicate and the average is used for the free swell rate of the sample material.

Determination of the Coating Caliper and Coating Caliper Uniformity

Elastomeric coatings on water-swellable polymers or materials as used herein can typically be investigated by standard scanning electron microscopy, preferably environmental scanning electron microscopy (ESEM) as known to those skilled in the art. In the following method the ESEM evaluation is also used to determine the average coating caliper and the coating caliper uniformity of the coated water-swellable polymers/materials via cross-section of the materials.

Equipment model: ESEM XL 30 FEG (Field Emission Gun)

ESEM setting: high vacuum mode with gold covered samples to obtain also images at low magnification (35×) and ESEM dry mode with LFD (large Field Detector which detects ~80% Gaseous Secondary Electrons +20% Secondary Electrons) and bullet without PLA (Pressure Limiting Aperture) to obtain images of the coating/shells as they are (no gold coverage required).

Filament Tension: 3 KV in high vacuum mode and 12 KV in ESEM dry mode.

Pressure in Chamber on the ESEM dry mode: from 0.3 Torr to 1 Torr on gelatinous samples and from 0.8 to 1 Torr for other samples.

Samples of coated water-swellable material or polymers or of uncoated polymers can be observed after about 1 hour at ambient conditions (20 C, 80% relative humidity) using the standard ESEM conditions/equipment.

Then, the same samples can be observed in high vacuum mode. Then the samples can be cut via a cross-sectional cut with a Teflon blade (Teflon blades are available from the AGAR scientific catalogue (ASSING) with reference code T5332), and observed again under vacuum mode.

The coatings have different morphology than the uncoated water-swellable polymers and the coatings are clearly visible in the ESEM images, in particular when observing the cross-sectional views.

The average coating caliper is determined then by analyzing at least 5 particles of the water-swellable material or coated water-swellable polymer and determining 5 average calipers, an average per particle (by analyzing the cross-section of each particle and measuring the caliper of the coating in at least 3 different areas) and taking then the average of these 5 average calipers.

The uniformity of the coating is determined by determining the minimum and maximum caliper of the coating via ESEM of the cross-sectional cuts of at least 5 different particles and determining the average (over 5) minimum and average maximum caliper and the ratio thereof.

If the coating is not clearly visible in ESEM, then staining techniques known to the skilled in the art that are specific for the coating applied may be used such as enhancing the contrast with osmium tetraoxide, potassium permanganate and the like, e.g., prior to using the ESEM method.

Method to Determine the Theoretical Equivalent Shell Caliper of the Water-swellable Material Herein If the amount of coating agent comprised in the water-swellable material is known, a theoretical equivalent average caliper may be determined as defined below.

This method calculates the average caliper of a coating layer or shell on the water-swellable material herein, under the assumption that the water-swellable material is to be monodisperse and spherical (which may not be the case in practice).

Key Parameters

|  | Symbol |
|---|---|
| INPUT Parameter |  |
| Mass Median Particle Size of the water-swellable polymer(AGM) prior to coating (also called "average diameter") | D_AGM_dry |
| Intrinsic density of the base water-swellable bulk polymer (without coating) | Rho_AGM_intrinsic |
| Intrinsic density of the phase-separating elastomeric polymer (coating or shell only) | Rho_polymer shell |
| Coating (shell) Weight Fraction of the Coated water-swellable polymer (Percent of coating as percent of total coated water-swellable polymer) | c_shell_per_total |
| OUTPUT Parameters |  |
| Average coating caliper if the water-swellable polymer is monodisperse and spherical | d_shell |
| Mass Median Particle Size of the Coated water-swellable polymer ("average diameter after coating") | D_AGM_coated |
| Coating Weight Ratio as Percent of Polymer Coating in percent of uncoated water-swellable polymer weight | c_shell_to_bulk |

Formulas
(note: in this notation: all c which are in percent have ranges of 0 to 1 which is equivalent To 0 to 100%.)

$$d\_shell := \frac{D\_AGM\_dry}{2} \cdot \left[\left[1 + \frac{c\_shell\_per\_total}{(1 - c\_shell\_per\_total)} \cdot \frac{Rho\_AGM\_intrinsic}{Rho\_polymer\_shell}\right]^{\frac{1}{3}} - 1\right]$$

$$D\_coated\_AGM := D\_AGM\_dry + 2 \cdot d\_shell$$

$$c\_shell\_to\_bulk := \frac{c\_shell\_per\_total}{1 - c\_shell\_per\_total}$$

EXAMPLE

| D_AGM_dry: = 0.4 mm (400 µm); Rho_AGM_intrinsic: = Rho_polymer_shell: = 1.5 g/cc |||||||||
|---|---|---|---|---|---|---|---|---|
| C_shell_per_total [%] | 1 | 2 | 5 | 10 | 20 | 30 | 40 | 50 |
| C_shell_to_bulk [%] | 1.0 | 2.0 | 5.3 | 11 | 25 | 43 | 67 | 100 |
| d_shell [µm] | 0.7 | 1.4 | 3.4 | 7.1 | 15 | 25 | 37 | 52 |
| D_Coated_AGM [µm] | 401 | 403 | 407 | 414 | 431 | 450 | 474 | 504 |

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent structure comprising water-swellable material that comprises a plurality of water-swellable polymer particles coated with a coating agent, wherein said coating agent comprises an elastomeric material that is phase-separating and has at least a first phase with a first glass transition temperature $Tg_1$ and a second phase with a second glass transition temperature $Tg_2$ wherein said absorbent structure is a part of a disposable absorbent article selected from the group consisting of infant diapers, training pants, adult incontinent articles, sanitary napkins, panty-liners, interlabial articles, and bandages, wherein said coating agent comprises at least one block copolymer selected from the group consisting of polyurethane-co-polyethers, polyurethane-co-polyesters, polyurethane/urea-co-polyethers, polyurethane/urea-co-polyesters, polystyrene block copolymers and blends thereof and is present in the form of a continuous shell around at least a portion of one or more of said water-swellable polymer particles, said shell having an average caliper of 1 µm to 50 µm.

2. An absorbent structure according to claim 1 wherein the difference between $Tg_1$ and $Tg_2$ is at least 30° C.

3. An absorbent structure according to claim 1, wherein said elastomeric phase-separating material has a $Tg_1$ of less than 20° C. and a $Tg_2$ of more than 50° C.

4. An absorbent structure according to claim 1, wherein the elastomeric phase separating material has a molecular weight of at least 50 kDa.

5. An absorbent structure according to claim 1 wherein said shell has a ratio of smallest to largest caliper of from 1:1 to 1:3.

6. An absorbent structure according to claim 1, wherein said coating agent is wet-extensible and has a wet-elongation at break of at least 400% and a tensile stress at break in the wet state of at least 1 MPa.

7. An absorbent structure according to claim 6 wherein the coating agent has, in the wet state, a wet secant elastic modulus at 400% elongation ($SM_{wet400\%}$) of at least 0.5 MPa.

8. An absorbent article according to claim 6, wherein the coating agent has, in the dry state, a dry secant modulus at 400% elongation ($SM_{dry400\%}$) such that the ratio of $SM_{wet400\%}$ to $SM_{dry400\%}$ is between 1.4 to 1.0 to 0.6 to 1.0.

9. A disposable absorbent article comprising a topsheet and a backsheet and having disposed therebetween an absorbent structure comprising water-swellable material that comprises a plurality of water-swellable polymer particles, coated with a coating agent, wherein said coating agent comprises an elastomeric material that is phase-separating and has at least a first phase with a first glass transition temperature $Tg_1$ and a second phase with a second glass transition temperature $Tg_2$, and wherein said coating agent comprises at least one block copolymer selected from the group consisting of polyurethane-co-polyethers, polyurethane-co-polyesters, polyurethane/urea-co-polyethers, polyurethane/urea-co-polyesters, polystyrene block copolymers and blends thereof and is present in the form of a continuous shell around at least a portion of one or more of said water-swellable polymer particles, said shell having an average caliper of 1 μm to 50 μm.

* * * * *

UNITED STATES PATENT AND TRADEMARK OFFICE
CERTIFICATE OF CORRECTION

PATENT NO. : 7,517,586 B2 Page 1 of 1
APPLICATION NO. : 10/911912
DATED : April 14, 2009
INVENTOR(S) : Fossum et al.

It is certified that error appears in the above-identified patent and that said Letters Patent is hereby corrected as shown below:

Column 19

Line 36, after the $H_4$ delete "°" and insert --O--.

Line 37, after the $H_6$ delete "°" and insert --O--.

Column 31

Line 9, delete "Ti" and insert --Tm--.

Signed and Sealed this

Twenty-second Day of September, 2009

David J. Kappos
*Director of the United States Patent and Trademark Office*